(12) United States Patent
Tsushima

(10) Patent No.: US 10,463,345 B2
(45) Date of Patent: Nov. 5, 2019

(54) ULTRASOUND SIGNAL PROCESSING DEVICE AND ULTRASOUND DIAGNOSTIC DEVICE

(71) Applicant: Konica Minolta, Inc., Tokyo (JP)

(72) Inventor: Mineo Tsushima, Kyoto-fu (JP)

(73) Assignee: KONICA MINOLTA, INC., Tokyo (JP)

(*) Notice: Subject to any disclaimer, the term of this patent is extended or adjusted under 35 U.S.C. 154(b) by 339 days.

(21) Appl. No.: 14/923,591

(22) Filed: Oct. 27, 2015

(65) Prior Publication Data

US 2016/0120503 A1   May 5, 2016

(30) Foreign Application Priority Data

Oct. 29, 2014   (JP) .................................. 2014-220560
Oct. 22, 2015   (JP) .................................. 2015-207909

(51) Int. Cl.
A61B 8/00   (2006.01)
A61B 8/08   (2006.01)
(Continued)

(52) U.S. Cl.
CPC ........ A61B 8/5207 (2013.01); G01S 7/52047 (2013.01); G01S 15/8915 (2013.01);
(Continued)

(58) Field of Classification Search
None
See application file for complete search history.

(56) References Cited

U.S. PATENT DOCUMENTS 5,598,206 A * 1/1997 Bullis ...................... G01S 15/32
                                                          348/81
5,924,993 A * 7/1999 Hadjicostis ......... G01S 15/8922
                                                          600/447

(Continued)

FOREIGN PATENT DOCUMENTS

JP   2004-283265 A   10/2004
JP   2009-240700 A   10/2009
(Continued)

OTHER PUBLICATIONS

M. Itou, et al; Ultrasound Diagnostic Device; Corona Publishing Co., Ltd; Aug. 26, 2002; pp. 42-45.
(Continued)

Primary Examiner — Hovhannes Baghdasaryan
(74) Attorney, Agent, or Firm — Lucas & Mercanti, LLP

(57) ABSTRACT

Ultrasound signal processing device including: transmitter causing transmission array composed of all or some transducer elements of ultrasound probe to transmit ultrasound; reception aperture setter designating reception array having center position corresponding to center position of transmission array; transmission time calculator calculating, for each of measurement points arranged within area of reach of ultrasound, transmission time from transmission of ultrasound until arrival of ultrasound at measurement point; reception time calculator calculating reception time from reflection of ultrasound at measurement point until arrival of ultrasound at reception transducer element; delay amount calculator calculating total propagation time being sum of transmission time and reception time, and calculating delay amount for reception transducer element based on total propagation time; delay processor specifying reception signal value corresponding to delay amount, from reception signal sequence corresponding to reception transducer element; and adder generating acoustic line signal for measurement point based on specified reception signal value.

20 Claims, 16 Drawing Sheets

(51) Int. Cl.
   *G01S 15/89* (2006.01)
   *G01S 7/52* (2006.01)
   *G10K 11/34* (2006.01)

(52) U.S. Cl.
   CPC ........ *G01S 15/8997* (2013.01); *G10K 11/346* (2013.01); *A61B 8/54* (2013.01)

(56) References Cited

U.S. PATENT DOCUMENTS

| | | | | |
|---|---|---|---|---|
| 5,966,169 | A * | 10/1999 | Bullis | G01S 15/8993 348/81 |
| 6,535,666 | B1 * | 3/2003 | Dogan | G01S 3/74 385/12 |
| 2001/0020130 | A1 | 9/2001 | Gee | G01S 7/52046 600/443 |
| 2001/0039381 | A1 * | 11/2001 | Burns | A61B 8/06 600/443 |
| 2002/0120196 | A1 * | 8/2002 | Dubberstein | G10K 11/346 600/447 |
| 2002/0133074 | A1 * | 9/2002 | Chiao | G01S 7/52038 600/437 |
| 2004/0039285 | A1 * | 2/2004 | Ustuner | A61B 8/0825 600/459 |
| 2004/0225218 | A1 * | 11/2004 | Guracar | G01S 7/52085 600/443 |
| 2005/0068221 | A1 * | 3/2005 | Freeman | G01S 7/52028 341/161 |
| 2005/0101867 | A1 * | 5/2005 | Johnson | A61B 8/14 600/459 |
| 2009/0326377 | A1 | 12/2009 | Hirama | |
| 2010/0030076 | A1 * | 2/2010 | Vortman | A61N 7/02 600/439 |
| 2011/0164466 | A1 * | 7/2011 | Hald | G01H 3/125 367/8 |
| 2016/0174938 | A1 | 6/2016 | Shinta | |
| 2016/0243381 | A1 * | 8/2016 | Alford | A61N 7/00 |
| 2017/0042510 | A1 | 2/2017 | Ikeda | |

FOREIGN PATENT DOCUMENTS

| | | |
|---|---|---|
| WO | 2015025655 A1 | 3/2017 |
| WO | 2015166867 A1 | 4/2017 |

OTHER PUBLICATIONS

S. I. Nikolov, et al; Virtual ultrasound sources in high resolution ultrasound imaging; Proc, SPIE—Progress in biomedical optics and imaging; vol. 3; 2002; pp. 395-405.

Notice of Reasons for Refusal, Patent Application No. 2015-207909, dated May 7, 2019, 5 Pages.

Notice of Reasons for Refusal, Patent Application No. 2018-110239, dated Apr. 2, 2019, 5 Pages.

M. Itou, et al; Ultrasound Diagnostic Equipment Corona Publishing Co., Ltd; Aug. 26, 2002; pp. 42-45.

S. I. Nekolov. et al; Virtual ultrasound sources in high resolution ultrasound imaging; Pros. SPIE—Progress in biomedical optics and imaging; vol. 3; 2002; pp 395-405.

* cited by examiner

ULTRASOUND SIGNAL PROCESSING DEVICE AND ULTRASOUND DIAGNOSTIC DEVICE

CROSS REFERENCE TO RELATED APPLICATION

This Application claims the priority of Japanese Patent Application No. 2014-220560 filed on Oct. 29, 2014 and Japanese Patent Application No. 2015-207909 filed on Oct. 22, 2015, both applications are incorporated by reference herein.

BACKGROUND OF THE INVENTION (1) Field of the Invention

The present disclosure is related to an ultrasound signal processing device, and an ultrasound diagnostic device utilizing the ultrasound signal processing device. In particular, the present disclosure relates to beam forming in an ultrasound signal processing device.

(2) Description of the Related Art

Typically, an ultrasound diagnostic device transmits ultrasound towards the inside of a subject via an ultrasound probe (referred to in the following as a "probe"), and receives reflected ultrasound (an echo) via the probe. The reflected ultrasound is generated within the subject due to different tissues in the subject having different acoustic impedances. Further, an ultrasound diagnostic device generates an ultrasound tomographic image based on electric signals acquired through the reception of the reflected ultrasound, and displays the ultrasound tomographic image on a monitor (referred to in the following as a "display unit"). The ultrasound tomographic image shows the structures of tissues inside the subject. Ultrasound diagnostic devices are widely used for the shape diagnosis of living bodies, for having low invasiveness and achieving real-time observation of tissues through tomographic images and the like.

A typical method applied in conventional ultrasound diagnostic devices for reception beam forming (i.e., forming signals based on received reflected ultrasound (echo signals)) is so-called delay-and-sum (DAS) beam forming. One example of delay-and-sum beam forming can be found disclosed in pages 42-45 of "Ultrasound Diagnostic Device", written by Masayasu Itou and Tsuyoshi Mochizuki and published by Corona Publishing Co., Ltd (Aug. 26, 2002).

FIG. 16 is a schematic illustrating reception beam forming in a conventional ultrasound diagnostic device. The conventional ultrasound diagnostic device illustrated in FIG. 16 includes a probe 201 and a reception beam former 202. The probe 201 includes a plurality of ultrasound transducer elements (referred to in the following as "transducer elements") 201a that receive ultrasound reflection (echo signals) from the subject. The reception beam former 202 electrically converts the reflected ultrasound received by the transducer elements 201a into analog electronic signals, converts the analog electronic signals into digital electronic signals through some amplification and A/D conversion, and performs delaying and summing of the digital electronic signals. The reception beam former 202 includes a plurality of delaying units 2021, and an adding unit 2022. The delaying units 2021 are each associated with a corresponding one of the transducer elements 201a, and performs amplification, A/D conversion, and delaying with respect to an electric signal. The adding unit 2022 provides signals output from the delay units 2021 with weights referred to as so-called apodization weights, and sums the weighted signals. The reception beam former 202 generates and outputs an acoustic line signal for a measurement point located along the central axis of the transmitted ultrasound beam. In specific, the reception beam former 202 generates the acoustic line signal by each of the delaying units 2021 performing delaying with respect to an electric signal based on reflected ultrasound obtained by the corresponding transducer element 201a, and by the adding unit 2022 summing the delayed electric signals obtained from the delaying units 2021. Typically, the delay amount that each delaying unit 2021 applies is based on the distance between the corresponding transducer element 201a and the measurement point, which is located along the central axis of the transmitted ultrasound beam as discussed above.

In specific, suppose that: P denotes a measurement point that is at a given depth inside the subject and that is located along the central axis of the transmitted ultrasound beam; C denotes a transducer element, among the plurality of transducer elements, that is closest to the measurement point P; dc denotes the distance between the measurement point P and the transducer element C; m denotes a transducer element other than the transducer element C; dm denotes the distance between the measurement point P and the transducer element m; and cs denotes ultrasound velocity. Here, the time point at which reflected ultrasound from the measurement point P arrives at the transducer element m is later than the time point at which reflected ultrasound from the measurement point P arrives at the transducer element C by (dm/cs−dc/cs). Thus, by calculating the time point at which reflected ultrasound from the measurement point P arrives at the transducer element C, the time point at which reflected ultrasound from the measurement point P arrives at the transducer element m can be calculated based on this difference (dm/cs−dc/cs). As such, each delaying unit 2021 specifies a reception signal for the corresponding transducer element 201a by considering the difference between arrival times of reflected ultrasound, and the adding unit 2022 generates an acoustic line signal by summing the reception signals specified by the delaying units 2021.

SUMMARY OF THE INVENTION

Problems to be Solved by the Invention

Here, it should be noted that the conventional reception beam forming method disclosed in "Ultrasound Diagnostic Device" discussed above has the following problem. The conventional reception beam forming method is capable of acquiring high quality ultrasound images with high resolution and low noise around a transmission focal point. A transmission focal point is a point at a given depth in the subject where the wavefront of transmitted ultrasound converges. Meanwhile, the conventional reception beam forming method has difficulty in acquiring high quality ultrasound images from areas within an ultrasound irradiation area that are far from the transmission focal point.

In view of such technical problems, the present disclosure provides an ultrasound signal processing device and an ultrasound diagnostic device utilizing the ultrasound signal processing device that are capable of generating high quality ultrasound images (i.e., ultrasound images with high resolution and low noise) from the entire ultrasound irradiation area, including areas far from the transmission focal point.

Means for Solving the Problems

One aspect of the present disclosure is an ultrasound signal processing device that causes an ultrasound probe having a plurality of transducer elements to transmit ultrasound towards a subject to acquire ultrasound reflected from the inside of the subject, generates a reception signal from the reflected ultrasound, and generates an acoustic line signal from the reception signal. The ultrasound signal processing device includes: an ultrasound signal processing circuit that functions as: a transmitter performing an ultrasound transmission session of causing a transmission transducer element array composed of all or some of the transducer elements to transmit ultrasound; a receiver generating a plurality of reception signal sequences, one for each of the transducer elements, each of the reception signal sequences generated based on reflected ultrasound that a corresponding one of the transducer elements receives in response to the transmission of the ultrasound; a first reception aperture setter designating a first reception transducer element array composed of some of the transducer elements and having a center position corresponding to a center position of the transmission transducer element array; a transmission time calculator performing, for each of a plurality of predetermined measurement points arranged within an assumed area of reach of the ultrasound inside the subject, a calculation of transmission time that is a time period from transmission of the ultrasound until arrival of the ultrasound at the measurement point; a first reception time calculator performing, for each of the measurement points, a calculation of reception time for each first reception transducer element in the reception transducer element array, the reception time being a time period from reflection of the ultrasound at the measurement point until arrival of the ultrasound at the first reception transducer element; a first delay amount calculator performing, for each of the measurement points, (i) a calculation of total propagation time for each first reception transducer element, the total propagation time being a sum of the transmission time and the reception time for the first reception transducer element, and (ii) a calculation of a delay amount for each first reception transducer element based on the total propagation time for the first reception transducer element; a first delay processor performing, for each of the measurement points, a specification of a reception signal value for each first reception transducer element, the specified reception signal value being a reception signal value corresponding to the delay amount for the first reception transducer element, from among reception signal values composing one of the reception signal sequences that corresponds to the first reception transducer element; and a first adder generating a first acoustic line signal for each of the measurement points, based on the specified reception signal values for the first reception transducer elements specified with respect to the measurement point.

BRIEF DESCRIPTION OF THE DRAWINGS

These and the other objects, advantages and features of the technology pertaining to the present disclosure will become apparent from the following description thereof taken in conjunction with the accompanying drawings, which illustrate specific embodiments of the technology pertaining to the present disclosure.

In the drawings.

DESCRIPTION OF THE PREFERRED EMBODIMENT

Figure 1:
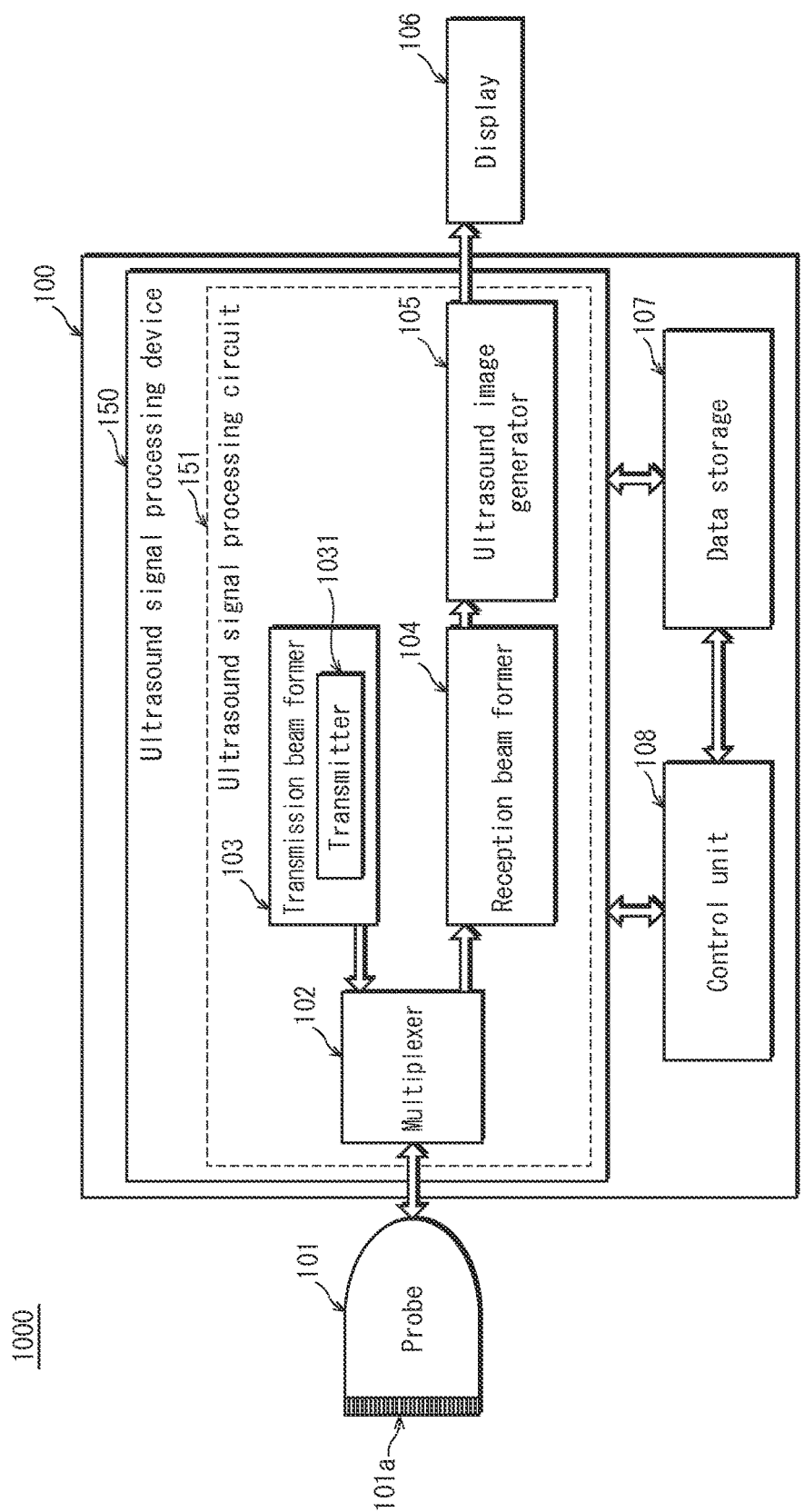
FIG. 1 is a functional block diagram illustrating the structure of an ultrasound diagnostic device 100 pertaining to embodiment 1.

The following describes embodiments of the technology pertaining to the present disclosure.

<How Inventors Arrived at Aspects of Present Disclosure>

The present inventor carried out extensive research for improving resolution and signal-to-noise ratio (SNR) of ultrasound images generated by ultrasound diagnostic devices.

The conventional ultrasound diagnostic device disclosed in "Ultrasound Diagnostic Device" performs transmission beam forming (i.e., transmission of ultrasound by a plurality of transducer elements towards the inside of the subject) such that a transmitted ultrasound beam converges (focuses) at a predetermined depth inside the subject. When performing transmission beam forming in such a manner, the ultrasound beam has high definition when a measurement point P is at or near the transmission focal point, due to the ultrasound beam being relatively focused at or near the transmission focal point. Further, the S/N ratio (here, S denotes echo from measurement point P, and N denotes signals from other areas inside the subject) of ultrasound reflection (echo signals) acquired from such a measurement point is also high, due to high spatial energy density at the measurement point. This results in an acoustic line signal with high resolution and high S/N ratio being acquired, and ultimately, in a high quality ultrasound image being acquired. Meanwhile, even if the measurement point P is located along the central axis of the transmitted ultrasound beam, if the measurement point P is far from the transmission focal point, obtaining a high quality ultrasound image is difficult due to an acoustic line signal acquired from such a measurement point having low resolution and low S/N ratio.

Further, in the conventional ultrasound diagnostic device, the measurement point P is always set along the central axis of the transmitted ultrasound beam. Accordingly, reception beam forming is naturally performed by using only reflected ultrasound from measurement points along the central axis of the transmitted ultrasound beam, without using reflected ultrasound from other areas of the ultrasound irradiation area. Due to this, one ultrasound transmission event generates only one acoustic line signal along the central axis of the transmitted ultrasound beam, and thus, reflected ultrasound is not utilized in an efficient manner.

Meanwhile, a reception beam forming method is being proposed that utilizes a so-called synthetic aperture method to yield high quality images not only from the transmission focal point but also from areas other than the transmission focal point. One example of reception beam forming utilizing the synthetic aperture method can be found disclosed in pages 395 through 405 of "Virtual Ultrasound Sources in High Resolution Ultrasound Imaging", S. I. Nikolov and J. A. Jensen, in Proc, SPIE—Progress in Biomedical Optics and Imaging, Vol. 3, 2002. According to this method, delaying is performed taking into consideration both a propagation path of ultrasound and the amount of time required for reflected ultrasound to arrive at a transducer element by travelling along the propagation path. Thus, the method achieves reception beam forming making use of not only reflected ultrasound from near the transmission focal point but also reflected ultrasound from areas of the ultrasound irradiation area other than near the transmission focal point. Due to this, the method enables generating, from one ultrasound transmission event, acoustic line signals covering the entire ultrasound irradiation area, including areas far from the transmission focal point. In addition, the synthetic aperture method enables setting a virtual transmission focal point based on multiple reception signals acquired for one measurement point P through multiple transmission sessions. Thus, the synthetic aperture method enables acquiring an ultrasound image with higher resolution and higher S/N ratio than the reception beam forming method disclosed in "Ultrasound Diagnostic Device".

However, even when adopting a reception beam forming method based on the synthetic aperture method, there are cases where a high quality ultrasound image cannot be acquired depending upon examination target part characteristics, e.g., what part of the subject is the examination-target part, the type and level of the disorder affecting the examination-target part, etc. In such cases, it is necessary to perform at least one of selecting an appropriate reception beam forming method, adjusting the reception beam forming method being utilized, and switching from one reception beam forming method to another, depending upon examination-target part characteristics. This leads to a decrease in examination efficiency.

In view of such problems, the present inventor conducted extensive research and consideration concerning the reason why ultrasound images with sufficient image quality cannot be acquired when the examination-target part has certain characteristics. Through such research and consideration, the present inventor has arrived at the conception that setting a reception aperture covering a vast measurement area and in some cases apodization covering a vast measurement area, while improving spatial resolution over the entirety of an image, does not necessarily yield a high S/N ratio. Further, the present inventor has arrived at the conception that, in order to acquire an ultrasound image with high image quality irrespective of examination-target part characteristics, it is necessary to achieve high spatial resolution at local areas in images, while at the same time achieving uniform spatial resolution over wide areas in images. In view of the above, the present inventor conducted further research and consideration for a technology achieving both high spatial resolution at local areas and uniform spatial resolution over wide areas in images. The ultrasound signal processing device and the ultrasound diagnostic device including the ultrasound signal processing device, each of which pertaining to one aspect of the present disclosure, result from such research and consideration.

The following describes the ultrasound signal processing device and the ultrasound diagnostic device including the ultrasound signal processing device, each of which pertaining to one aspect of the present disclosure in detail.

<Aspects of Present Disclosure>

One aspect of the present disclosure is an ultrasound signal processing device that causes an ultrasound probe having a plurality of transducer elements to transmit ultrasound towards a subject to acquire ultrasound reflected from the inside of the subject, generates a reception signal from the reflected ultrasound, and generates an acoustic line signal from the reception signal. The ultrasound signal processing device includes: an ultrasound signal processing circuit that functions as: a transmitter performing an ultrasound transmission session of causing a transmission transducer element array composed of all or some of the transducer elements to transmit ultrasound; a receiver generating a plurality of reception signal sequences, one for each of the transducer elements, each of the reception signal sequences generated based on reflected ultrasound (echo signals) that a corresponding one of the transducer elements receives in response to the transmission of the ultrasound; a first reception aperture setter designating a first reception transducer element array composed of some of the transducer elements and having a center position corresponding to a center position of the transmission transducer element array; a transmission time calculator performing, for each of a plurality of predetermined measurement points arranged within an assumed area of reach of the ultrasound inside the subject, a calculation of transmission time that is a time period from transmission of the ultrasound until arrival of the ultrasound at the measurement point; a first reception time calculator performing, for each of the measurement points, a calculation of reception time for each first reception transducer element in the reception transducer element array, the reception time being a time period from reflection of the ultrasound at the measurement point until arrival of the ultrasound at the first reception transducer element; a first delay amount calculator performing, for each of the measurement points, (i) a calculation of total propagation time for each first reception transducer element, the total propagation time being a sum of the transmission time and the reception time for the first reception transducer element, and (ii) a calculation of a delay amount for each first reception transducer element based on the total propagation time for the first reception transducer element; a first delay processor performing, for each of the measurement points, a specification of a reception signal value for each first reception transducer element, the specified reception signal value being a reception signal value corresponding to the delay amount for the first reception transducer element, from among reception signal values composing one of the reception signal sequences that corresponds to the first reception transducer element; and a first adder generating a first acoustic line signal for each of the measurement points, based on the specified reception signal values for the first reception transducer elements specified with respect to the measurement point. The first adder may calculate a sum of the specified reception signal values for the first reception transducer elements.

In the ultrasound signal processing device pertaining to one aspect of the present disclosure, the ultrasound signal processing circuit may also function as: a first weight calculator calculating a weight sequence for the first reception transducer element array, the weight sequence including the greatest weight for a first reception transducer element at the center position of the first reception transducer element array, and the first adder may generate the first acoustic signal line for each of the measurement points by, for each first reception transducer element, multiplying the specified reception signal value for the first reception transducer element specified with respect to the measurement point by a weight included in the weight sequence that corresponds to the first reception transducer element, and by summing products yielded by performing the multiplication for each first reception transducer element.

In the ultrasound signal processing device pertaining to one aspect of the present disclosure, the ultrasound signal processing circuit may also function as: a second reception aperture setter performing, for each of the measurement points, a designation of a second reception transducer element array composed of some of the transducer elements and having a center position corresponding to one of the transducer elements that is closest to the measurement point; a second reception time calculator performing, for each of the measurement points, a calculation of reception time for each second reception transducer element in the second reception transducer element array, the reception time being a time period from reflection of the ultrasound at the measurement point until arrival of the ultrasound at the second reception transducer element; a second delay amount calculator performing, for each of the measurement points, (i) a calculation of total propagation time for each second reception transducer element, the total propagation time being a sum of the transmission time and the reception time for the second reception transducer element, and (ii) a calculation of a delay amount for each second reception transducer element based on the total propagation time for the second reception transducer element; a second delay processor performing, for each of the measurement points, a specification of a reception signal value for each second reception transducer element, the specified reception signal value being a reception signal value corresponding to the delay amount for the second reception transducer element, from among reception signal values composing one of the reception signal sequences that corresponds to the second reception transducer element; and a second adder generating a second acoustic line signal for each of the measurement points, based on the specified reception signal values for the second reception transducer elements specified with respect to the measurement point. The second adder may calculate a sum of the specified reception signal values for the second reception transducer elements.

In the ultrasound signal processing device pertaining to one aspect of the present disclosure, the ultrasound signal processing circuit may also function as: a second weight calculator calculating a weight sequence for the second reception transducer element array, the weight sequence including the greatest weight for a second reception transducer element at the center position of the second reception transducer element array, and the second adder generates the second acoustic signal line for each of the measurement points by, for each second reception transducer element, multiplying the specified reception signal value for the second reception transducer element specified with respect to the measurement point by a weight included in the weight sequence that corresponds to the second reception transducer element, and by summing products yielded by performing the multiplication for each second reception transducer element.

In the ultrasound signal processing device pertaining to one aspect of the present disclosure, the ultrasound signal processing circuit may also function as: a Tx/Rx selection signal calculator selecting one of the first acoustic line signal and the second acoustic line signal; and an output selector that outputs one of the first acoustic line signal and the second acoustic line signal in accordance with the result of the selection by the Tx/Rx selection signal calculator.

In the ultrasound signal processing device pertaining to one aspect of the present disclosure, the Tx/Rx selection signal calculator may perform the selection based on input performed by an operator of the ultrasound signal processing device or based on a predetermined condition.

In the ultrasound signal processing device pertaining to one aspect of the present disclosure, the Tx/Rx selection signal calculator may perform the selection based on a characteristic of the plurality of reception signal sequences.

In the ultrasound signal processing device pertaining to one aspect of the present disclosure, the Tx/Rx selection signal calculator may determine whether or not a puncture needle is being used with respect to the subject and select the first acoustic line signal when determining that a puncture needle is being used with respect to the subject.

In the ultrasound signal processing device pertaining to one aspect of the present disclosure, the Tx/Rx selection signal calculator, when detecting an object causing specular reflection based on the plurality of reception signal sequences, may determine that a puncture needle is being used with respect to the subject and selects the first acoustic line signal.

In the ultrasound signal processing device pertaining to one aspect of the present disclosure, the Tx/Rx selection signal calculator may perform the selection based on at least one of the first acoustic line signal and the second acoustic line signal. In the ultrasound signal processing device pertaining to one aspect of the present disclosure, the ultrasound signal processing circuit may also function as: a Tx/Rx weight calculator calculating a weight for the first acoustic line signal and a weight for the second acoustic line signal; and an output mixer performing a calculation of multiplying each of the first acoustic line signal and the second acoustic line signal by a corresponding weight and summing the products yielded by performing the multiplication with respect to each of the first acoustic line signal and the second acoustic line signal, and outputting a result of the calculation In the ultrasound signal processing device pertaining to one aspect of the present disclosure, the Tx/Rx weight calculator may perform, for each of the measurement points, a calculation of the weight corresponding to the first acoustic line signal and the weight corresponding to the second acoustic line signal based on input performed by an operator of the ultrasound signal processing device or based on a predetermined condition.

In the ultrasound signal processing device pertaining to one aspect of the present disclosure, the Tx/Rx weight calculator may calculate the weight corresponding to the first acoustic line signal and the weight corresponding to the second acoustic line signal based on a characteristic of the plurality of reception signal sequences.

In the ultrasound signal processing device pertaining to one aspect of the present disclosure, the Tx/Rx weight calculator may calculate the weight corresponding to the first acoustic line signal and the weight corresponding to the second acoustic line signal based on the first acoustic line signal and the second acoustic line signal.

In the ultrasound signal processing device pertaining to one aspect of the present disclosure, the characteristic of the plurality of reception signal sequences may be calculated based on the reception signal value for a first reception transducer element with the smallest delay amount in the first reception transducer element array and the reception signal value for a second reception transducer element with the smallest delay amount in the second transducer element array.

In the ultrasound signal processing device pertaining to one aspect of the present disclosure, the transmission transducer element array may be composed of only some of the transducer elements of the ultrasound probe, the transmitter may perform a plurality of ultrasound transmission sessions while changing the transducer elements of the ultrasound probe included in transmission transducer element array each time, and the first adder may generate the first acoustic line signal for each of the measurement points by synthesizing a plurality of first acoustic line signals for the measurement point, each of which acquired based on one of the ultrasound transmission sessions.

In the ultrasound signal processing device pertaining to one aspect of the present disclosure, the transmission transducer element array may be composed of only some of the transducer elements of the ultrasound probe, the transmitter may perform a plurality of ultrasound transmission sessions while changing the transducer elements of the ultrasound probe included in transmission transducer element array each time, the first adder may generate the first acoustic line signal for each of the measurement points by synthesizing a plurality of first acoustic line signals for the measurement point, each of which acquired based on one of the ultrasound transmission sessions, and the second adder may generate the second acoustic line signal for each of the measurement points by synthesizing a plurality of second acoustic line signals for the measurement point, each of which acquired based on one of the ultrasound transmission sessions.

In the ultrasound signal processing device pertaining to one aspect of the present disclosure, the transmitter may perform a plurality of ultrasound transmission sessions until all of the transducer elements of the ultrasound probe have transmitted ultrasound at least once One aspect of the present disclosure is an ultrasound diagnostic device configured so that the ultrasound probe is connectable thereto.

Embodiment 1

Overall Structure

The following describes an ultrasound diagnostic device pertaining to embodiment 1, with reference to the accompanying drawings.

FIG. 1 illustrates functional blocks of the ultrasound diagnostic device pertaining to embodiment 1 (an ultrasound diagnostic system 1000). As illustrated in FIG. 1, the ultrasound diagnostic system 1000 includes: a probe 101; an ultrasound diagnostic device 100; and a display unit 106. The probe 101 includes a plurality of transducer elements 101a. Each of the transducer elements 101a transmits ultrasound towards the subject and receives reflected ultrasound (echo signals). The ultrasound diagnostic device 100 causes the probe 101 to perform transmission/reception of ultrasound, and generates an ultrasound image based on signals output from the probe 101. The display unit 106 displays the ultrasound image on any display device provided thereto. The probe 101 and the display unit 106 are separately connectable to the ultrasound diagnostic device 100. FIG. 1 illustrates the ultrasound diagnostic device 100 with the probe 101 and the display unit 106 connected thereto. Alternatively, the ultrasound diagnostic device 100 may include therein the probe 101 and the display unit 106.

<Structure of Ultrasound Diagnostic Device 100>

The ultrasound diagnostic device 100 includes a multiplexer 102; a transmission beam former 103; and a reception beam former 104. The multiplexer 102 selects one or more of the transducer elements 101a for ultrasound transmission and one or more of the transducer elements 101a for ultrasound reception. The multiplexer 102 may select different ones of the transducer elements 101a for ultrasound transmission and ultrasound reception. Further, the multiplexer 102 provides the transducer elements 101a for ultrasound transmission with input, and receives output from the transducer elements 101a for ultrasound reception. The transmission beam former 103 controls timings of application of a high voltage for ultrasound transmission to each of the transducer elements 101a for ultrasound transmission. The reception beam former 104 performs some amplification and A/D conversion on electric signals yielded by the transducer elements 101a for ultrasound reception, based on reflected ultrasound received by the probe 101, and performs reception beam forming to generate an acoustic line signal. In addition, the ultrasound diagnostic device 100 includes an ultrasound image generator 105; a data storage 107; and a control unit 108. The ultrasound image generator 105 generates an ultrasound image based on signals output from the reception beam former 104. The data storage 107 stores the acoustic line signal output from the reception beam former 104 and the ultrasound image output from the ultrasound image generator 105. The control unit 108 controls each of the other constituent elements of the ultrasound diagnostic device 100.

Among the constituent elements of the ultrasound diagnostic device 100, the multiplexer 102, the transmission beam former 103, the reception beam former 104, and the ultrasound image generator 105 constitute an ultrasound signal processing circuit 151, and the ultrasound signal processing circuit 151 constitutes an ultrasound signal processing device 150.

Each constituent element of the ultrasound diagnostic device 100, for example, each of the multiplexer 102, the transmission beam former 103, the reception beam former 104, the ultrasound image generator 105, and the control unit 108 may be implemented by using a hardware circuit such as a field-programmable gate array (FPGA), an application-specific integrated circuit (ASIC), or the like. Alternatively, each of the constituent elements may be implemented by using a combination of software and a programmable device such as a central processing unit (CPU) or any processor. Each of such constituent elements may be implemented as one circuit component, or as an aggregate of a plurality of circuit components. Further, a plurality of such constituent elements may be implemented by using one circuit component, or as an aggregate of a plurality of circuit components.

The data storage 107 is a computer-readable recording medium. For example, the data storage 107 may be implemented by using a flexible disk, a hard disk, an MO, a DVD, a DVD-RAM, or a semiconductor memory. Alternatively, the data storage 107 may by an external storage device connected to the ultrasound diagnostic device 100.

Note that the ultrasound diagnostic device 100 pertaining to the present embodiment need not have the structure illustrated in FIG. 1. For example, the ultrasound diagnostic device 100 need not include the multiplexer 102. Further, the probe 101 may have built-in therein a part or the entirety of each of the transmission beam former 103, the reception beam former 104, and the like.

<Structure of Main Part of Ultrasound Diagnostic Device 100>

The ultrasound diagnostic device 100 pertaining to the present embodiment is characterized for including the transmission beam former 103 and the reception beam former 104. The transmission beam former 103 causes the transducer elements 101a of the probe 101 to transmit ultrasound. The reception beam former 104 performs computation with respect to electric signals acquired through the reception of reflected ultrasound by the probe 101, and generates an acoustic line signal used in forming an ultrasound image. Accordingly, the present disclosure focuses on the structure and the functions of each of the transmission beam former 103 and the reception beam former 104. Note that components other than the transmission beam former 103 and the reception beam former 104 may have structures and functions similar to those in conventional ultrasound diagnostic devices. In other words, the ultrasound diagnostic device 100 may be implemented by replacing beam formers in a conventional ultrasound diagnostic device with the beam formers pertaining to the present embodiment.

The following describes the structure of each of the transmission beam former 103 and the reception beam former 104.

1. Transmission Beam Former 103

The transmission beam former 103 is connected to the probe 101, via the multiplexer 102. However, note that the multiplexer is not a mandatory element in the present disclosure. The transmission beam former 103 controls timings of application of high voltage with respect to ones of the transducer elements 101a composing a transmission aperture Tx. The transmission aperture Tx is an array of transducer elements (first transducer element array) composed of all or some of the transducer elements 101a of the probe 101. Note that in the following, the term "transmission transducer element" is used to refer to transducer elements composing the transmission aperture Tx, or in other words, the first transducer element array. The transmission beam former 103 includes a transmitter 1031.

The transmitter 1031 performs transmission processing. The transmission processing involves supplying a transmission signal having a pulsar waveform to each of the transmission transducer elements. A transmission transducer element receiving a transmission signal transmits an ultrasound beam. The transmitter 1031 supplies transmission signals to the transmission transducer elements based on transmission control signals output from the control unit 108. In specific, the transmitter 1031 includes, for example, a clock generation circuit, a pulse generation circuit, and a delay circuit. The clock generation circuit generates a clock signal specifying the transmission timing of ultrasound beams. The pulse generation circuit generates pulse signals for driving the transmission transducer elements. The delay circuit performs focus processing so that ultrasound beams are appropriately focused. In specific, the delay circuit sets a delay time for each transmission transducer element, and delays the transmission of the ultrasound beam from the transmission transducer element by the corresponding delay time.

The transmitter 1031 repetitively performs ultrasound transmission while shifting the transmission aperture Tx in the transducer element array direction each time, so that all of the transducer elements 101a of the probe 101 transmit ultrasound. Further, the transmitter 1031 outputs information indicating the positions of transmission transducer elements composing the transmission aperture Tx to the data storage 107, via the control unit 108. For example, supposing that the probe 101 has one hundred and ninety two (192) transducer elements 101a in total, the number of transmission transducer elements composing the transmission aperture Tx may be twenty (20) to one hundred (100). In the following, ultrasound transmission by the transmitter 1031, performed by using one transmission aperture (i.e., one set of transmission transducer elements of the predetermined number) is referred to as a transmission event.

Figure 2:
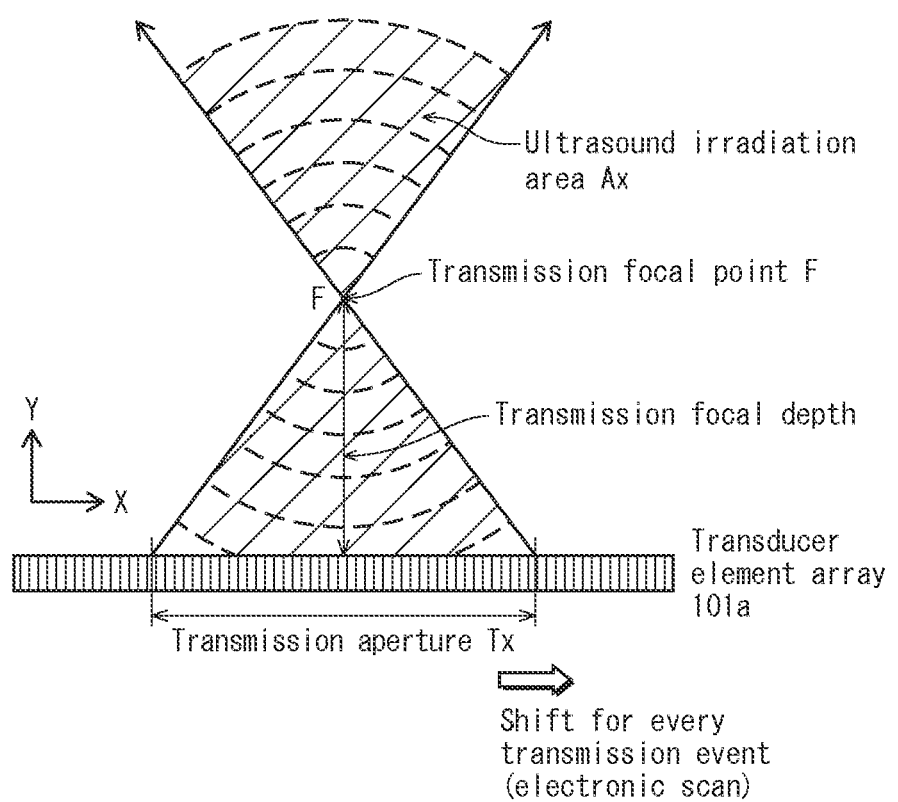
FIG. 2 is a schematic illustrating a propagation path of ultrasound transmitted from transmission beam former 103 in the ultrasound diagnostic device 100.

FIG. 2 is a schematic illustrating a propagation path of an ultrasound beam formed by the transmission beam former 103. FIG. 2 illustrates a transmission aperture Tx for one transmission event (i.e., a first transducer element array composed of transmission transducer elements 101a that contribute to ultrasound transmission in the transmission event). Further, the transmission-array direction length of the transmission aperture Tx is considered the length of the transmission aperture Tx.

The transmission beam former 103 controls ultrasound transmission by the transmission transducer elements such that a transmission transducer element closer to the center position of the transmission aperture Tx transmits ultrasound later in the transmission event. Due to this, a wavefront of ultrasound transmitted from the transmission transducer elements composing the transmission aperture Tx converges at one point at a certain focal depth in the subject (i.e., the transmission focal point F). Note that the depth of the focal point F can be set as desired or required. After converging at the focal point F, the wavefront of the transmitted ultrasound expands as before converging at the focal point F. Thus, the transmitted ultrasound waves propagate through an hourglass-shaped area whose bottom is defined by the transmission aperture Tx and which is partitioned from other areas inside the subject by two straight lines intersecting at the transmission focal point F. That is, ultrasound transmitted from the transmission aperture Tx propagates in the following manner. As the transmitted ultrasound advances in the depth direction from the transmission aperture Tx, the width thereof (length along horizontal axis (X axis) in FIG. 2) gradually decreases until reaching the minimum width at the transmission focal point F. Then, as the transmitted ultrasound advances further in the depth direction from the transmission focal point F (i.e., as the ultrasound advances in the upward direction in FIG. 2), the width thereof increases (i.e., the ultrasound spreads out). In the following, the hourglass-shaped area described above, which is indicated by hatching in slanted lines in FIG. 2, is referred to as an ultrasound irradiation area Ax.

2. Reception Beam Former 104

Figure 3:
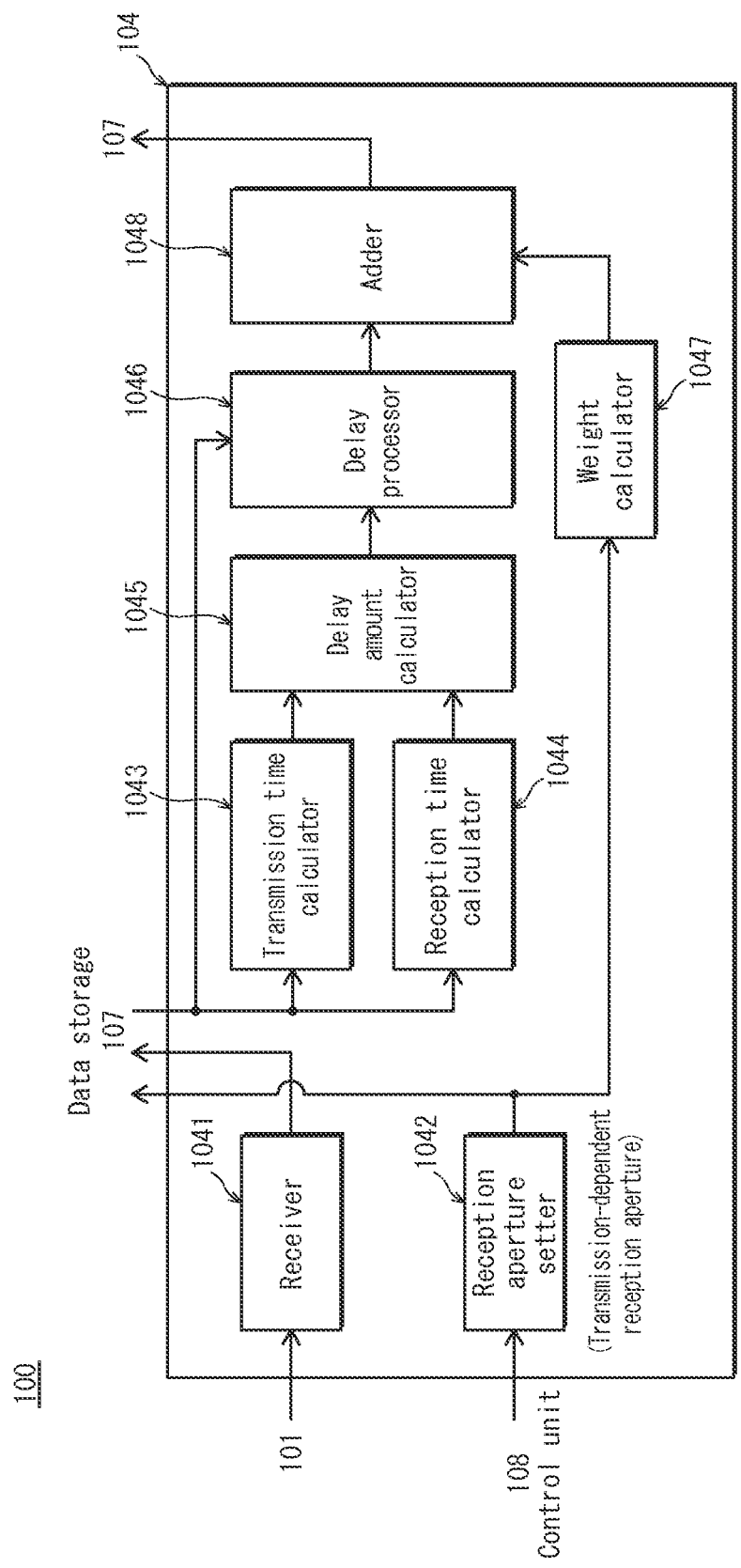
FIG. 3 is a functional block diagram illustrating the structure of a reception beam former 104 in the ultrasound diagnostic device 100.

The reception beam former 104 generates an acoustic line signal from electric signals acquired by a plurality of transducer elements 101a. The transducer elements 101a acquire the electric signals based on reflected ultrasound received by the probe 101. FIG. 3 is a functional block diagram illustrating the structure of the reception beam former 104. As illustrated in FIG. 3, the reception beam former 104 includes: a receiver 1041; a reception aperture setter 1042; a transmission time calculator 1043; a reception time calculator 1044; a delay amount calculator 1045; a delay processor 1046; a weight calculator 1047; and an adder 1048.

The following describes the structure of each functional block of the reception beam former 104.

(1) Receiver 1041

The receiver 1041 is connected to the probe 101, via the multiplexer 102. However, note that the multiplexer is not a mandatory element in the present disclosure. For each transmission event, the receiver 1041 generates reception signals (RF signals). The receiver 1041 generates the reception signals by first amplifying electric signals acquired through the probe 101 receiving reflected ultrasound, and then performing A/D conversion on the amplified signals. The receiver 1041 performs the generation of reception signals each time a transmission event takes place, and outputs the reception signals to be stored in the data storage 107.

Here, the receiver 1041 generates one reception signal (RF signal) for each of some or all of the transducer elements 101a of the probe 101. In specific, a reception signal for a given transducer element is a digital signal yielded by performing A/D conversion on an electrical signal yielded through conversion of reflected ultrasound received by the transducer element, and is a sequence of signals along the ultrasound transmission direction (corresponding to the depth direction with respect to the subject) that are received by the transducer element.

As discussed above, in each transmission event, the transmitter 1031 causes transmission transducer elements composing the transmission aperture Tx, among the transducer elements 101a of the probe 101, each to transmit an ultrasound beam. Meanwhile, for each ultrasound transmission event, the receiver 1041 generates a reception signal sequence for each of some or all of the plurality of transducer elements 101a of the probe 101. The generation of the reception signal sequence for a given one of the transducer elements 101a is based on reflected ultrasound yielded by the given transducer element 101a. Here, it is preferable that the number of transducer elements receiving reflected ultrasound (i.e., the number of transducer elements for which the receiver 1041 generates a reception signal sequence) is greater than the number of transmission transducer elements composing the transmission aperture Tx. Further, all of the transducer elements 101a of the probe 101 may be used for receiving the reflected ultrasound.

Further, as already discussed above, the transmitter 1031 repetitively performs transmission events while shifting the transmission aperture Tx in the transducer element array direction each time, so that all of the transducer elements 101a of the probe 101 transmit ultrasound. Meanwhile, for each ultrasound transmission event, the receiver 1041 generates a reception signal sequence for each of the plurality of transducer elements used for receiving the reflected ultrasound, and stores the reception signal sequences to the data storage 107.

(2) Reception Aperture Setter 1042

The reception aperture setter 1042 is a circuit that sets, for each transmission event, a reception aperture Rx based on a control signal from the control unit 108. In specific, for each transmission event, the reception aperture setter 1042 selects some of the transducer elements 101a of the probe 101 as reception transducer elements forming a second transducer element array. Here, it should be noted that the center position of the second transducer element array (i.e., the reception aperture Rx) of a given transmission event matches the center position of the first transducer element array (i.e., the transmission aperture Tx) for the transmission event.

Figure 4:
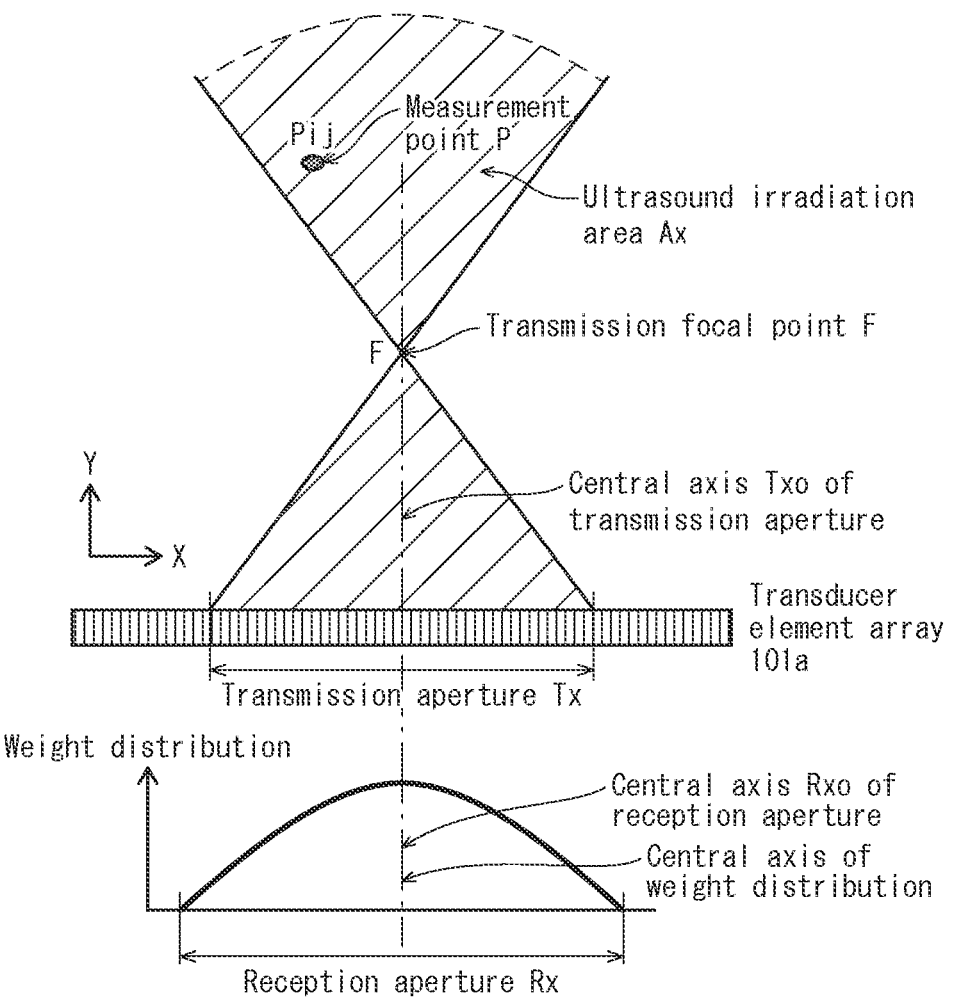
FIG. 4 is a schematic illustrating the relationship between a reception aperture Rx set by the reception beam former 104 and a transmission aperture Tx.

FIG. 4 is a schematic illustrating the relationship between the transmission aperture Tx for a given transmission event and the reception aperture Rx set by the reception beam former 104 for the transmission event. As illustrated in FIG. 4, in the present embodiment, the position of an axis Rxo passing through the center position of the reception aperture Rx corresponds to the position of an axis Txo passing through the center position of the transmission aperture Tx. Further, the reception aperture Rx is symmetric about the transmission focal point F (i.e., has the same number of apertures at both sides of the center position thereof in the transmission array direction). As such, as the transmission aperture Tx shifts in the transducer element array direction for each transmission event, the reception aperture Rx also shifts in the transducer element array direction, following the transmission aperture Tx.

In order to achieve utilizing reflected ultrasound from the entirety of the ultrasound irradiation area, the number of the reception transducer elements composing the reception aperture Rx for a given transmission event is, preferably, greater than or equal to the number of transmission transducer elements composing the transmission aperture Tx for the transmission event. For example, the number of reception transducer elements may be 32, 64, 96, 128, or 192.

The setting of the reception aperture Rx is performed for each transmission event. Due to this, the setting of the reception aperture Rx is repeated for the number of times transmission events are performed. Further, the setting of the reception aperture Rx may be performed each time a transmission event is performed as described above, or alternatively, reception apertures Rx for multiple transmission events having been performed may be set at once after the completion of the transmission events.

Further, the reception apparatus setter 1042 outputs information indicating the positions of the reception transducer elements composing the reception aperture Rx to the data storage 107, via the control unit 108.

The data storage 107, when the information indicating the positions of the reception transducer elements is input thereto, outputs the information along with reception signal sequences for the reception transducer elements to each of the transmission time calculator 1043, the reception time calculator 1044, and the delay processor 1046.

(3) Transmission Time Calculator 1043

The transmission time calculator 1043 is a circuit that calculates a transmission time for each measurement point P inside the subject. The transmission time is the amount of time required for transmitted ultrasound to arrive at each measurement point P. The transmission time calculator 1043 acquires information indicating the positions of the transmission transducer elements for a given transmission event from the data storage 107. Based on this information, the transmission time calculator 1043, for a measurement point Pij arranged within the ultrasound irradiation area Ax, calculates the transmission time required for transmitted ultrasound to arrive at the measurement point Pij.

Figure 5:
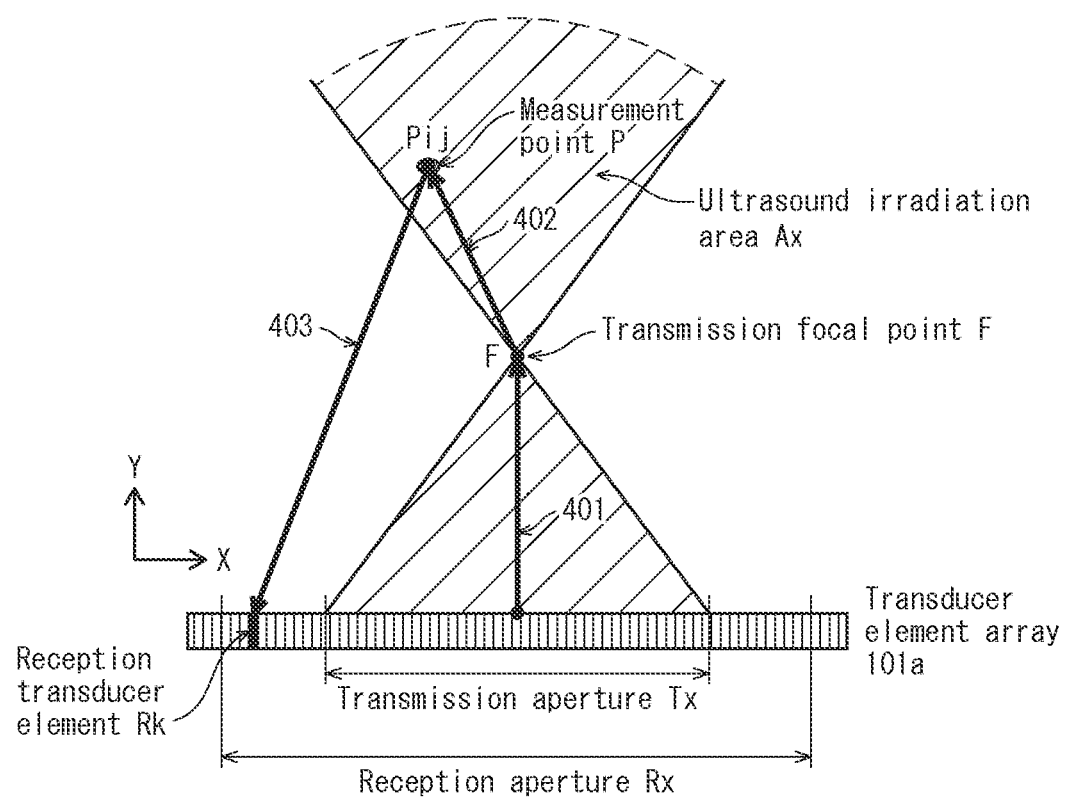
FIG. 5 is a schematic illustrating a propagation path of ultrasound that is transmitted from the transmission aperture Tx, is reflected at a measurement point Pij located at a given position within an ultrasound irradiation area Ax, and arrives at a transducer element included in the reception aperture Rx.

FIG. 5 is a schematic illustrating a propagation path of ultrasound that is transmitted from the transmission aperture Tx, is then reflected at the measurement point Pij arranged within the ultrasound irradiation area Ax, and finally arrives at a reception transducer element Rk of the reception aperture Rx. Following emission of ultrasound from the transmission aperture Tx, the wavefront of the ultrasound converges at the transmission focal point F after proceeding along the path 401. Subsequently, the wavefront of the ultrasound expands and arrives at the measurement point Pij. When there is a change in acoustic impedance at the measurement point Pij, the transmitted ultrasound generates ultrasound reflection, which is received by the reception transducer element Rk of the reception aperture Rx. The transmission focal point F is preset in advance upon designing of the transmission beam former 103. Thus, the length of the path 402 from the transmission focal point F to the measurement point Pij can be calculated geometrically.

For each transmission event, the transmission time calculator 1043 calculates the transmission time for each measurement point Pij within the ultrasound irradiation area Ax. That is, the transmission time calculator 1043 calculates, for each measurement point Pij, the time required for transmitted ultrasound to arrive at the measurement point Pij. Further, the transmission time calculator 1043 outputs the transmission time so calculated to the delay amount calculator 1045.

(4) Reception Time Calculator 1044

The reception time calculator 1044 is a circuit that calculates a reception time required for ultrasound reflection from each measurement point P to arrive at each reception transducer element Rk of the reception aperture Rx. The reception time calculator 1044 acquires information indicating the positions of the reception transducer elements Rk for a given transmission event from the data storage 107. Based on this information, the reception time calculator 1044, for a measurement point Pij arranged within the ultrasound irradiation area Ax, calculates the reception time required for transmitted ultrasound to arrive at each reception transducer element Rk after being reflected at the measurement point Pij.

As already discussed above, transmitted ultrasound arriving at a measurement point Pij generates ultrasound reflection when there is a change in acoustic impedance at the measurement point Pij. The reflected ultrasound is then received by reception transducer elements Rk of the reception aperture Rx. As discussed above, the reception time calculator 1044 acquires information indicating the positions of the reception transducer elements Rk of the reception aperture Rx from the data storage 107. Accordingly, the reception time calculator 1044 is able to calculate the length of the path 403 from the measurement point Pij to each of the reception transducer elements Rk.

For one transmission event, the reception time calculator 1044 calculates the reception time for each measurement point P within the ultrasound irradiation area Ax. That is, the reception time calculator 1044 calculates, for each measurement point P, the time required for transmitted ultrasound to arrive at each reception transducer element Rk after being reflected at the measurement point P. Further, the reception time calculator 1044 outputs the reception time so calculated to the delay amount calculator 1045.

(5) Delay Amount Calculator 1045

The delay amount calculator 1045 is a circuit that calculates, for each reception transducer element Rk, a total propagation time based on the transmission time and the reception time for the reception transducer element Rk. Further, the delay amount calculator 1045 calculates, for each reception transducer element Rk, a delay amount to be applied to a reception signal sequence for the reception transducer element Rk. In specific, the delay amount calculator 1045 acquires, from the transmission time calculator 1043, the transmission time required for ultrasound waves to arrive at a measurement point Pij. Further, for each reception transducer element Rk, the delay amount calculator 1045, acquires from the reception time calculator 1044, the reception time required for ultrasound to be reflected at the measurement point Pij and arrive at the reception transducer element Rk. Then, the delay amount calculator 1045, for each reception transducer element Rk, calculates a total propagation time required for transmitted ultrasound to arrive at the reception transducer element Rk. Further, based on the difference between total propagation times for the reception transducer elements Rk, calculates a delay amount for each reception transducer element Rk. For each measurement point P within the ultrasound irradiation area Ax, the delay amount calculator 1045 calculates, for each reception transducer element Rk, the delay amount to be applied to a reception signal sequence for the reception transducer element Rk, and outputs the delay amounts to the delay processor 1046.

(6) Delay Processor 1046

The delay processor 1046 is a circuit that specifies, for each reception transducer element Rk, a reception signal based on reflected ultrasound from a measurement point Pij. In specific, for each reception transducer element Rk, the delay processor 1046 specifies a reception signal corresponding to the delay amount for the reception transducer element Rk from the reception signal sequence for the reception transducer element Rk. More specifically, for each transmission event, the delay processor 1046 acquires, for each reception transducer element Rk, information indicating the position of the reception transducer element Rk and the reception signal sequence for the reception transducer element Rk from the data storage 107, and the delay amount to be applied to the reception signal sequence of the reception transducer element Rk from the delay amount calculator 1045. Further, for each reception transducer element Rk, the delay processor 1046 specifies a reception signal based on reflected ultrasound from a measurement point Pij. In specific, the delay processor 1046 specifies, from the reception signal sequence for the reception transducer element Rk, a reception signal corresponding to a time point after subtraction of the delay amount for the reception transducer element Rk.

(7) Weight Calculator 1047

The weight calculator 1047 is a circuit that calculates a weight sequence (so-called reception apodization weight) for the reception transducer elements Rk, so that the maximum weight is set with respect to the reception transducer element located at the center position of the reception aperture Rx in the transducer element array direction.

As illustrated in FIG. 4, the weight sequence is a numerical sequence of weight coefficients that are to be applied to reception signals for the reception transducer elements composing the reception aperture Rx. The weight sequence indicates weights that are distributed symmetrically with respect to the transmission focal point F. As the shape of distribution of the weights indicated by the weight sequence, any shape is applicable, including but not limited to a hamming window, a hanning window, and a rectangular window. The weight sequence is set so that the maximum weight is set with respect to the reception transducer element located at the center position of the reception aperture Rx in the transducer element array direction, and the central axis of the weight distribution corresponds to the center axis Rxo of the reception aperture Rx. The weight calculator 1047 uses as input information indicating the positions of the reception transducer elements Rk, which is output from the data storage 107, and outputs the weight sequence for the reception transducer elements Rk to the adder 1048.

(8) Adder 1048

The adder 1048 is a circuit that generates a delay-and-sum acoustic line signal for each measurement point P, by using as input the specified reception signals for the reception transducer element Rk, which are output from the delay processor 1046, and summing together the specified reception signals. Alternatively, the adder 1048 may generate an acoustic line signal for each measurement point P by using as input the weight numerical sequence for the reception transducer elements Rk, which is output from the weighting calculator 1047, multiplying the specified reception signal for each reception transducer element Rk with a corresponding weight, and summing the weighted reception signals. Here, an acoustic line signal for an measurement point Pij is a delay-and-sum reception signal for the measurement point Pij. The adder 1048 sums the reception signals for the reception transducer elements Rk, after the reception signals have been put in the same phase by the delay processor 1046. Due to this, the adder 1048 is capable of increasing the S/N ratio of the reception signals received by the reception transducer elements Rk based on reflected ultrasound from the measurement point Pij, and reception signals for the measurement point Pij can be extracted.

As a result of one transmission event and processing accompanying the transmission event, an acoustic line signal is generated for each measurement point P within the ultrasound irradiation area Ax. Further, by repetitively performing transmission events while gradually shifting the transmission aperture Tx in the transducer element array direction each time, all of the transducer elements 101a in the probe 101 perform ultrasound transmission. Due to this, an acoustic line signal corresponding to one frame is generated. Here, a frame is a unit of signals necessary for forming one ultrasound image. Further, a plurality of acoustic lines signals that are generated from one transmission event, each of which corresponding to one of the measurement points P within the ultrasound irradiation area Ax, are referred to in the following as a sub-frame acoustic line signal.

The adder 1048, for each transmission event, generates a sub-frame acoustic line signal for each measurement point P within the ultrasound irradiation area Ax. Further, the adder 1048 outputs the sub-frame acoustic line signals so generated to be stored in the data storage 107.

<Operations>

Figure 6:
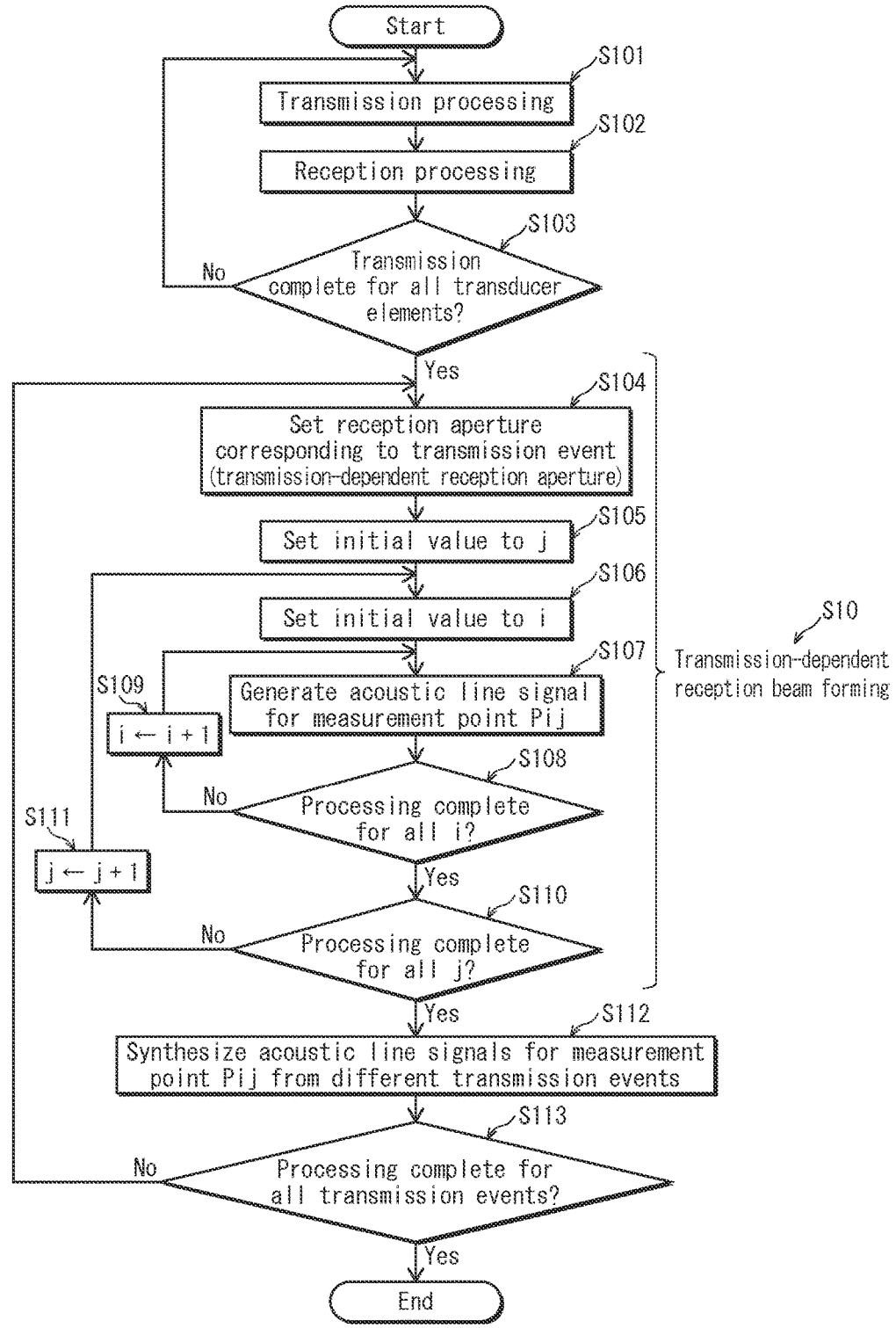
FIG. 6 is a flowchart illustrating the operations of the reception beam former 104 for beam forming.

The following describes the operations of the ultrasound diagnostic device 100 having the structure described up to this point. FIG. 6 is a flowchart illustrating beam forming by the reception beam former 104 in the ultrasound diagnostic device 100.

First, in Step S101, the transmitter 1031 performs transmission processing (a transmission event) of supplying a transmission signal causing transmission of an ultrasound beam to each transmission transducer element of the transmission aperture Tx.

In Step S102, the receiver 1041 generates reception signals based on electric signals yielded through the reception of reflected ultrasound by the probe 101, and outputs the reception signals to be stored in the data storage 107. Then, a determination is made of whether or not all transducer elements 101a of the probe 101 have performed ultrasound transmission (S103). When one or more of the transducer elements 101a have not yet performed ultrasound transmission, processing returns to Step S101, which results in another transmission event being executed by using the next transmission aperture Tx in the transducer element array direction. Meanwhile, when all of the transducer elements 101a have performed ultrasound transmission, processing proceeds to Step S104.

In Step S104, the reception aperture setter 1042 sets a reception aperture Rx for a transmission event by selecting reception transducer elements Rk composing a second transducer element array whose center position matches the center position of the first transducer element array for the corresponding transmission event.

Subsequently, coordinate values i and j indicating a position of a measurement point Pij in the ultrasound irradiation area Ax, which can be calculated from the transmission aperture Tx, are initialized (set to the respective minimum possible values in the ultrasound irradiation area Ax) (Steps S105 and S106). Subsequently, an acoustic line signal is generated for the measurement point Pij (Step S107).

Figure 7:
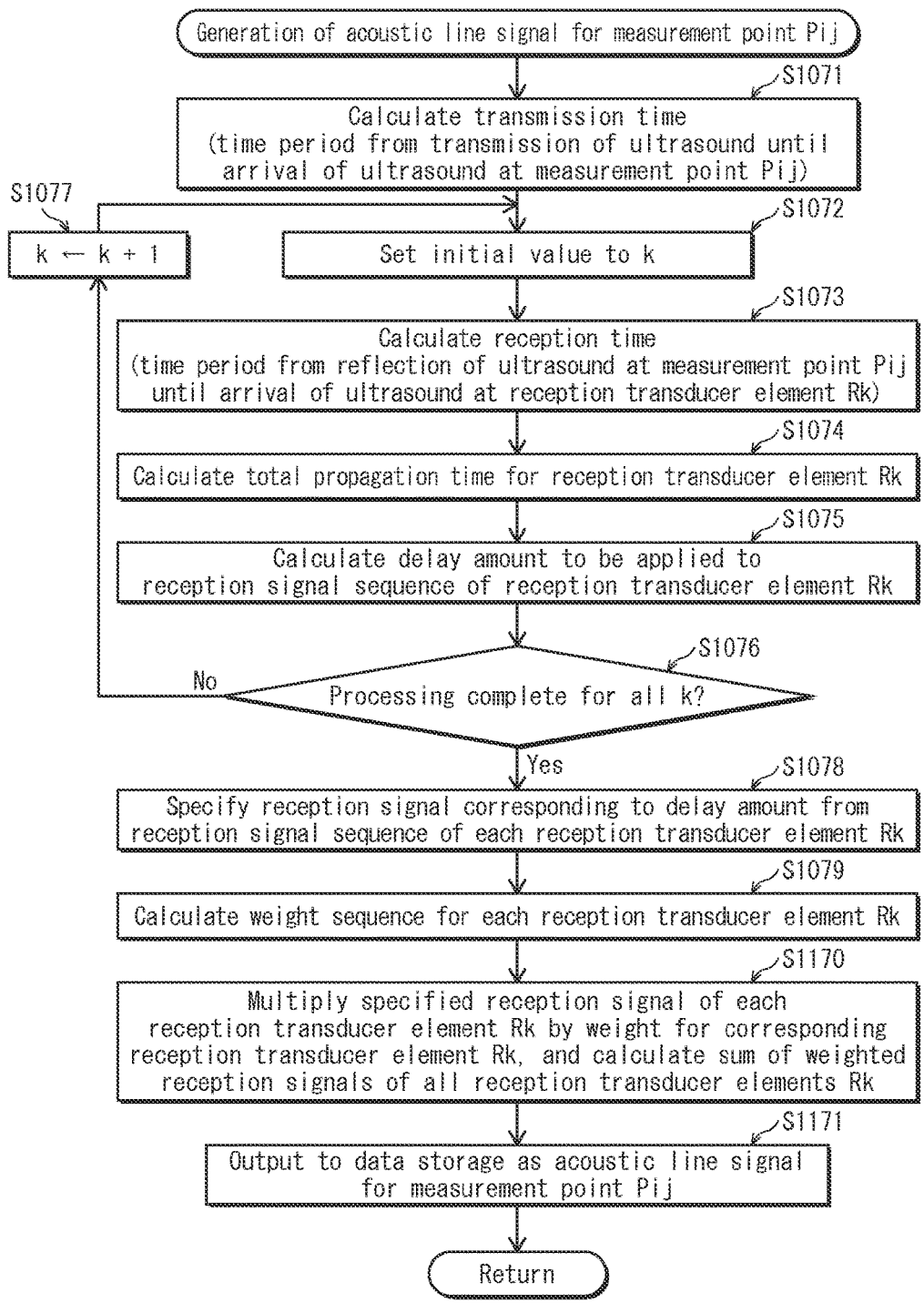
FIG. 7 is a flowchart illustrating the operations of the reception beam former 104 for generating an acoustic line signal for measurement point Pij.
Figure 8:
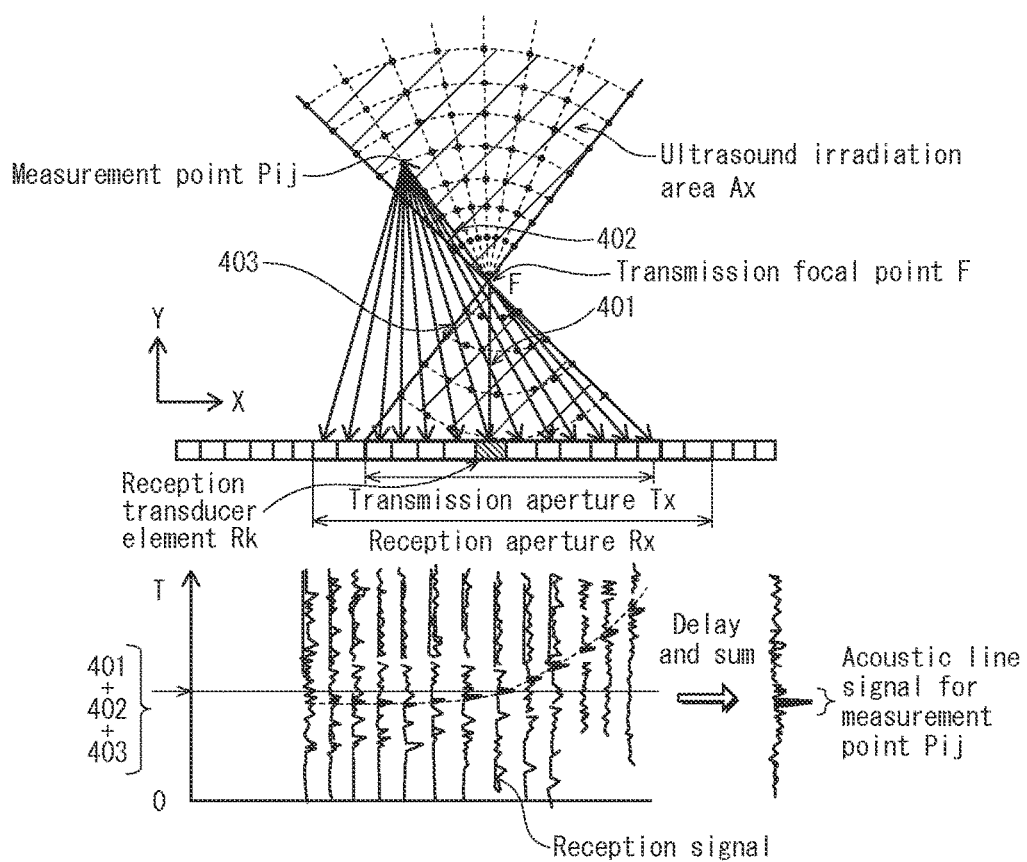
FIG. 8 is a schematic for explaining the operations of the reception beam former 104 for generating an acoustic line signal for measurement point Pij.

The following describes how the acoustic line signal for the measurement point Pij is generated in Step S107. FIG. 7 is a flowchart illustrating the operations of the reception beam former 104 for generating the acoustic line signal for the measurement point Pij. FIG. 8 is a schematic for explaining the operations of the reception beam former 104 for generating the acoustic line signal for the measurement point Pij.

First, in Step S1071, the transmission time calculator 1043 calculates, for the measurement point Pij within the ultrasound irradiation area Ax, a transmission time required for transmitted ultrasound to arrive at the measurement point Pij. The transmission time can be calculated by dividing, by ultrasound velocity (cs), the geometrically-calculable length of the path (401+402) starting from a reception transducer element, passing through the transmission focal point F, and arriving at the measurement point Pij.

Subsequently, value k, which indicates the position of a target reception transducer element of the reception aperture Rx, is initialized (set to the minimum possible value in the reception aperture Rx) (Step S1072). Then, the reception time for the reception transducer element Rk is calculated (Step S1073). The reception time is the time required for transmitted ultrasound to arrive at the reception transducer element Rk after being reflected at the measurement point Pij. Further, from a sum of the transmission time and the reception time, the total propagation time required for ultrasound transmitted from the transmission aperture Tx to arrive at the reception transducer element Rk after being reflected at the measurement point Pij is calculated (Step S1074). Further, based on the difference in total propagation time between different reception transducer elements Rk, the delay amount for the reception transducer element Rk is calculated (Step S1075).

Subsequently, a determination is performed of whether or not a delay amount has been calculated for every reception transducer element Rk composing the reception aperture Rx (Step S1076). When a delay amount has not yet been calculated for one or more of the reception transducer elements Rk, the value k is incremented (Step S1077), and a delay amount for another reception transducer element Rk is calculated (Step S1073). Meanwhile, when a delay amount has been calculated for every reception transducer element Rk composing the reception aperture Rx, processing proceeds to Step S1078. Note that at this point, a delay amount for the measurement point Pij has already been calculated for each reception transducer element Rk of the reception aperture Rx. The delay amount for a given reception transducer element Rk indicates delay with which reflected ultrasound from the measurement point Pij arrives at the reception transducer element Rk.

In Step S1078, the delay processor 1046, for each reception transducer element Rk, specifies a reception signal based on reflected ultrasound from the measurement point Pij. Here, the delay processor 1046 specifies, from a reception signal sequence corresponding to the reception transducer element Rk, a reception signal corresponding to a time point after subtraction of the delay amount for the reception transducer element Rk.

Subsequently, the weight calculator 1047 calculates a weight sequence for the reception transducer elements Rk of the current reception aperture Rx, so that the maximum weight is set with respect to the reception transducer element located at the center position of the reception aperture Rx in the transducer element array direction (S1079). Then, the adder 1048 generates an acoustic line signal for the measurement point Pij by multiplying the specified reception signal for each reception transducer element Rk by a weight corresponding to the reception transducer element Rk, and summing the weighted reception signals for the different reception transducer elements Rk (Step S1170). Following this, the adder 1048 outputs the acoustic line signal for the measurement point Pij to the data storage 107 to be stored in the data storage 107 (Step S1171).

Referring to FIG. 6 once again, subsequently, an acoustic line signal is generated for each measurement point P (each illustrated in FIG. 8 as a black dot) within the ultrasound irradiation area Ax by repeating Step S107 while incrementing the coordinate values i and j. Subsequently, a determination is performed of whether or not an acoustic line signal has been generated for every measurement point P arranged within the ultrasound irradiation area (Steps S108 and S110). When an acoustic line signal has not yet been generated for one or more measurement points Pij arranged within the ultrasound irradiation area Ax, an acoustic line signal is generated for another measurement point Pij (Step S107) by incrementing the coordinate values i and j (Steps S108 and S109). Meanwhile, when an acoustic line signal has already been generated for each measurement point P within the ultrasound irradiation area Ax, processing proceeds to Step S112. At this point, a sub-frame acoustic line signal has already been generated for each measurement point P within the ultrasound irradiation area Ax corresponding to one transmission event, and the sub-frame acoustic line signals have been output to and stored to the data storage 107.

In Step S112, a determination is made of whether there exists in the data storage 107 an acoustic line signal for the same measurement point Pij as the measurement point Pij for which an acoustic line signal has been generated in Step S107. When such an acoustic line signal does exist, the acoustic line signal for the measurement Pij in the data storage 107 has been generated through processing for a different transmission event. When such an acoustic line signal does exist in the data storage 107, the adder 1048 combines the acoustic line signal generated in Step S107 with the corresponding acoustic line signal stored in the data storage 107.

Subsequently, a determination is performed of whether or not sub-frame acoustic line signals have been generated for each transmission event having been performed (Step S113). When sub-frame acoustic line signals have not yet been generated for one or more transmission events, processing proceeds to Step S104, where setting of a reception aperture Rx corresponding to a transmission aperture Tx for a subsequent transmission event is performed. Meanwhile, when sub-frame acoustic line signals have been generated for every transmission event having been performed, processing is terminated.

<Effects>

In the ultrasound diagnostic device 100, whose structure is described up to this point, the reception aperture setter 1042 sets, for each transmission event, the reception aperture Rx by selecting reception transducer elements forming a second transducer element array whose center position corresponds to the center position of the first transducer element array for the transmission event. Due to this, the position of the central axis Rxo of the reception aperture Rx for a given transmission event corresponds to the central axis Txo of the transmission aperture Tx for the same transmission event. Further, when transmission events are repetitively performed, the transmission aperture Tx shifts in the transducer element array direction each time, and the reception aperture Rx also shifts in the transducer element array direction in synchronization with the transmission aperture Tx. In addition, reception beam forming may be performed by using a reception apodization having a symmetrical distribution at both sides of the central axis Txo in the transducer element array direction. Thus, a different reception aperture (or a different reception aperture and different apodization weight) is used to perform delay-and-sum for each transmission event. Accordingly, reception processing with respect to multiple transmission events can be performed by using a group of reception apertures (or a group of reception apertures and apodization weights) covering a vast measurement area and each differing in terms of time. Thus, uniform spatial resolution is achieved over a vast measurement area.

Further, the ultrasound diagnostic device 100 performs delaying based on the total propagation time, which is the time period from when ultrasound is transmitted from the transmission aperture Tx until the ultrasound is received by reception transducer elements Rk of the reception aperture Rx after passing through the transmission focal point F and being reflected at the measurement point P arranged within the ultrasound irradiation area Ax. This enables performing delay-and-sum processing focusing on each measurement point P arranged within the ultrasound irradiation area Ax, and generating an acoustic line signal for each measurement point P. This achieves generating, for one ultrasound transmission event, not only an acoustic line signal generated based on ultrasound reflection from an area of the ultrasound irradiation area along the central axis of the transmitted ultrasound beam, but also acoustic line signals generated based on ultrasound reflection from areas of the ultrasound irradiation area other than the rather narrow area along the central axis of the transmitted ultrasound beam, and thus, improves image quality (i.e., achieves high spatial resolution, low noise, etc.,) by enhancing the efficiency of use of transmitted ultrasound.

Further, the ultrasound diagnostic device 100, according to the synthetic aperture method, synthesizes acoustic line signals for the same measurement point P generated for different transmission events. This achieves the effect of performing, for multiple transmission events, virtual transmission focusing with respect to measurement points P that are located in depths other than that of the transmission focal point F. This further improves spatial resolution and S/N ratio.

Embodiment 2

In the ultrasound diagnostic device 100 pertaining to embodiment 1, the reception aperture Rx is set by selecting reception transducer elements forming a second transducer element array whose center position corresponds to the center position of the first transducer element array (i.e., the corresponding transmission aperture Tx). However, the configuration of the reception aperture Rx may be changed as necessary, as long as acoustic line signals for all measurement points P within the ultrasound irradiation area Ax can be generated by calculating total propagation times and performing delaying based on total propagation paths. As already discussed above, a total propagation time for a given reception transducer element Rk is the time required for ultrasound transmitted from the transmission aperture Tx to reach the reception transducer element Rk after passing through the transmission focal point F and being reflected at the measurement point P.

Embodiment 2 describes an ultrasound diagnostic device 100A. The ultrasound diagnostic device 100A includes a reception beam former 104A. The reception beam former 104A includes a reception aperture setter 1042A. The reception aperture setter 1042A sets, for each measurement point P, the reception aperture Rx so that the center position of the reception aperture Rx in the transducer element array direction corresponds to a transducer element that is spatially closest to the measurement point P. Other than the reception aperture setter 1042A, the constituent elements of the ultrasound diagnostic device 100A have the same structures and configurations as the corresponding constituent elements in the ultrasound diagnostic device 100 described in embodiment 1. Thus, description of such similar constituent elements is not provided in the following. That is, the ultrasound signal processing device of the ultrasound diagnostic device 100A is constituted of an ultrasound signal processing circuit including, in addition to the reception aperture setter 1042A, the multiplexer 102, the transmission beam former 103, and the ultrasound image generator 105.

<Structure>

Figure 9:
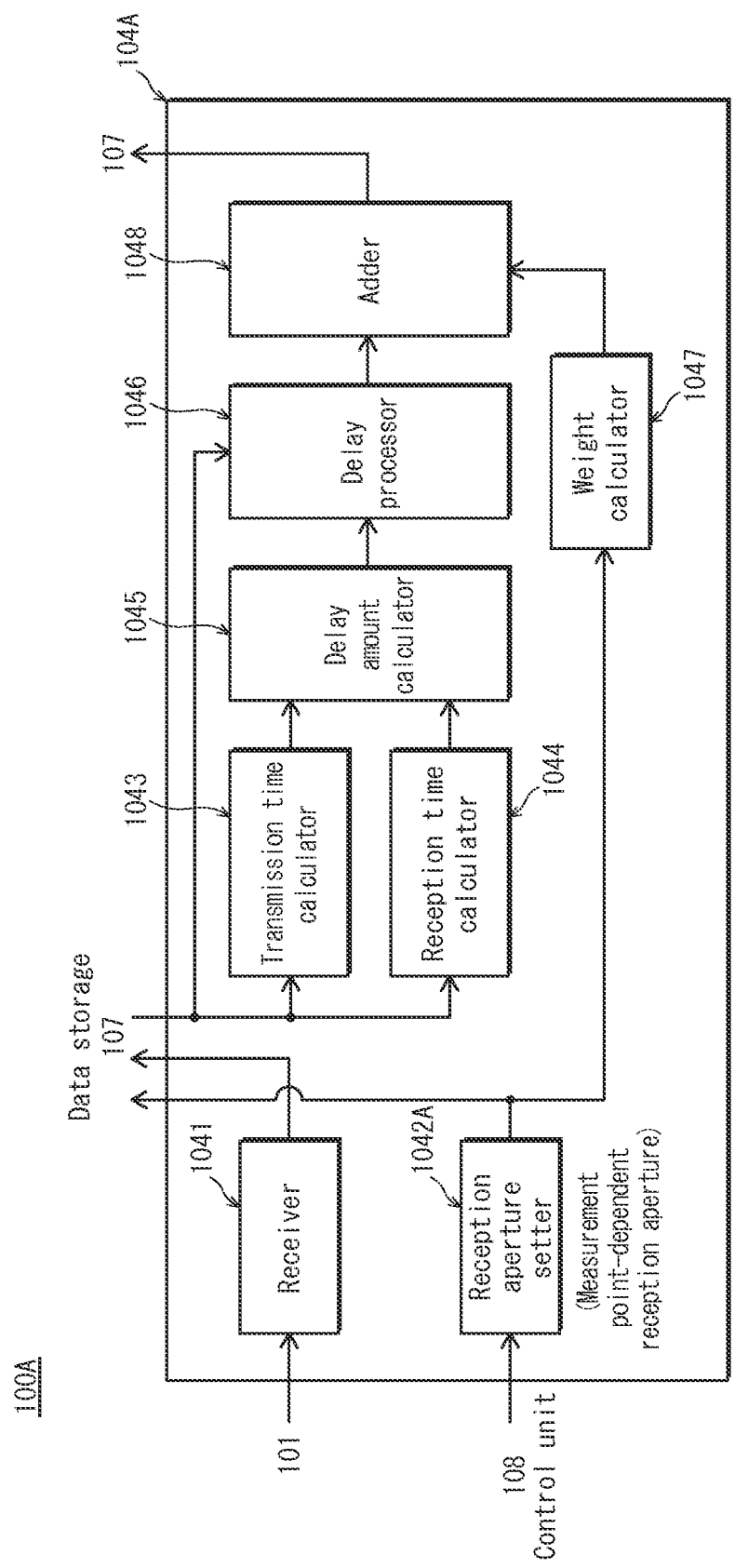
FIG. 9 is a functional block diagram illustrating the structure of a reception beam former 104A of an ultrasound diagnostic device 100A pertaining to embodiment 2.

The following describes the ultrasound diagnostic device 100A pertaining to embodiment 2, with reference to the accompanying drawings. FIG. 9 is a functional block diagram illustrating the structure of the reception beam former 104A of the ultrasound diagnostic device 100A. The ultrasound diagnostic device 100A differs from the ultrasound diagnostic device 100 for including the reception aperture setter 1042A, in place of the reception aperture setter 1042. Other than the reception aperture setter 1042A, the constituent elements of the ultrasound diagnostic device 100A have the same structures and configurations as the corresponding constituent elements in the ultrasound diagnostic device 100. Thus, description of such similar constituent elements is not provided in the following.

Figure 10:
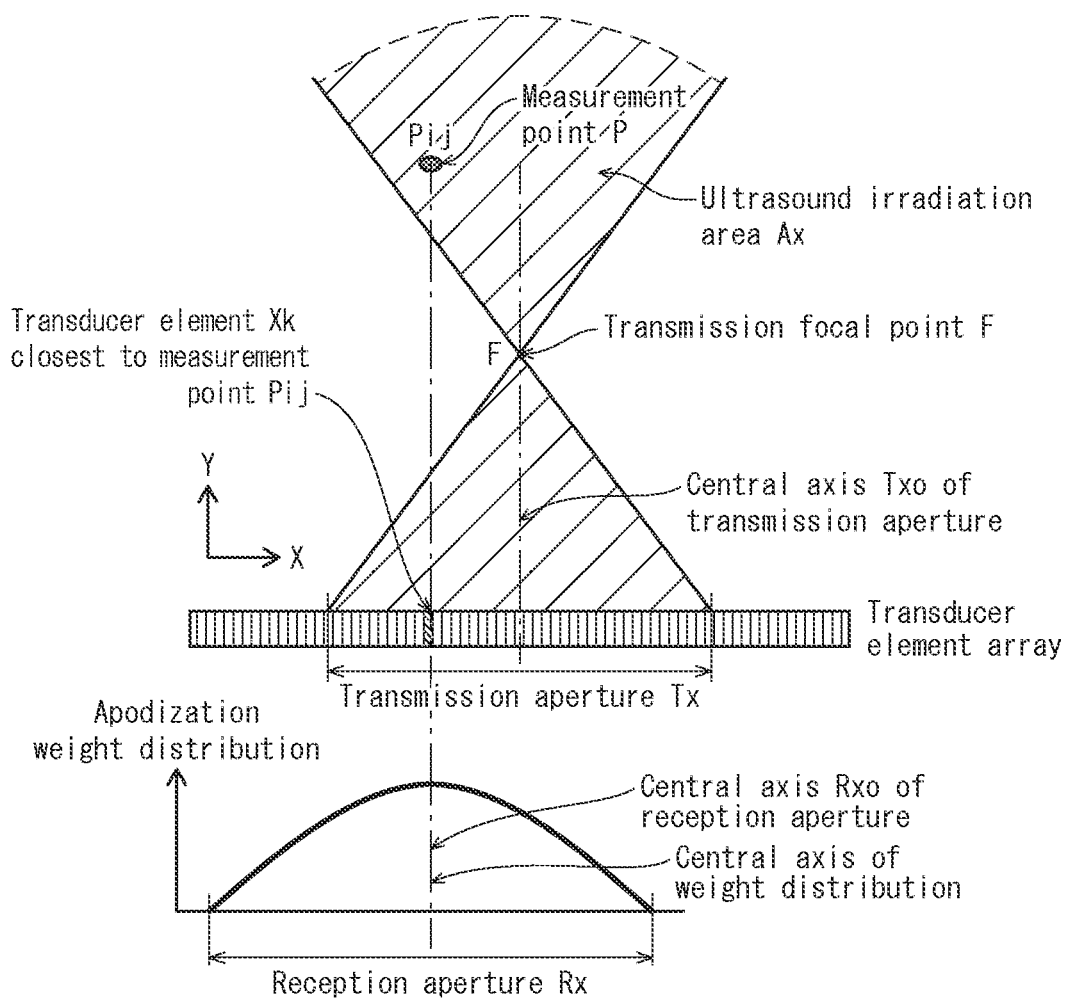
FIG. 10 is a schematic illustrating the relationship between a reception aperture Rx set by the reception beam former 104 and the transmission aperture Tx.

As already discussed above, the reception aperture setter 1042A sets, for each measurement point P, the reception aperture Rx so that the center position of the reception aperture Rx in the transducer element array direction corresponds to a transducer element that is spatially closest to the measurement point P. FIG. 10 is a schematic illustrating the relationship between the transmission aperture Tx and the reception aperture Rx, which is set by the reception beam former 104A as discussed above. As illustrated in FIG. 10, in embodiment 2, for a given measurement point Pij, the reception aperture Rx is set so that the center position of the reception aperture Rx in the transducer element array direction corresponds to a transducer element Xk that is spatially closest to the measurement point Pij. Further, a weight sequence (reception apodization weights) for the reception transducer elements Rk composing the reception aperture Rx is calculated so that the maximum weight is set with respect to the transducer element Xk (i.e., the reception transducer element Rk located at the center position of the reception aperture Rx in the transducer element array direction). The weight sequence indicates weights distributed symmetrically with respect to the transducer element Xk. As the shape of distribution of the weights indicated by the weight sequence, any shape is applicable, including but not limited to a hamming window, a hanning window, and a rectangular window.

Due to this, the position of the reception aperture Rx depends upon the position of the measurement point P, and does not change depending upon the position of the transmission aperture Tx, which shifts each time a transmission event is performed. That is, delay-and-sum processing for generating an acoustic line signal for a given measurement point Pij is always performed based on reception signal sequences acquired by reception transducer elements Rk composing the same reception aperture Rx. This means that with respect to the measurement point Pij, the same reception aperture Rx is used in delay-and-sum processing irrespective of transmission events.

<Operations>

Figure 11:
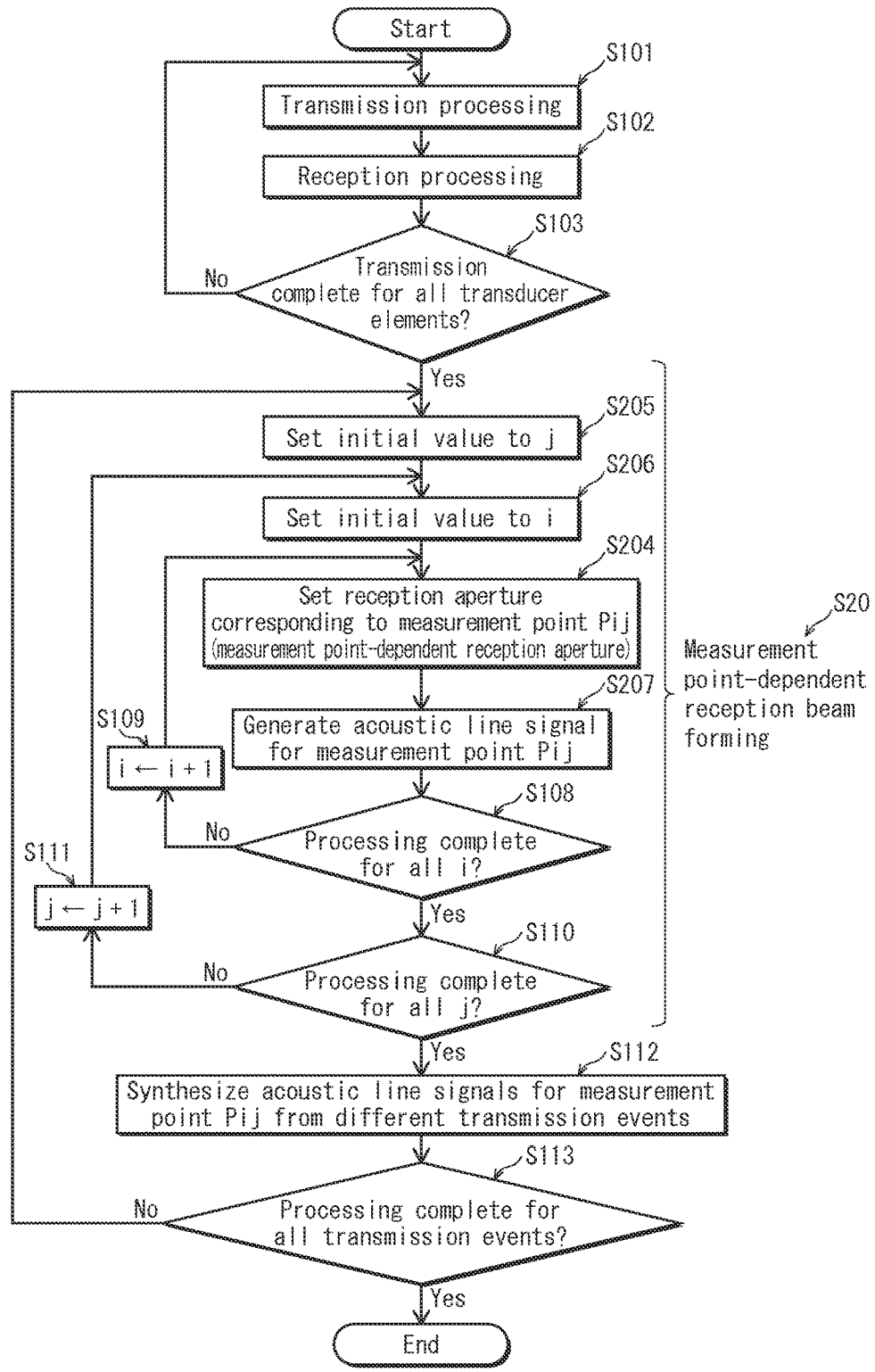
FIG. 11 is a flowchart illustrating the operations of the reception beam former 104A for beam forming.

FIG. 11 is a flowchart illustrating beam forming by the reception beam former 104A. The flowchart in FIG. 11 differs from the flowchart in FIG. 6 for measurement point-dependent beam forming (Step S20 (including Steps S204 through S211)) being performed in place of transmission-dependent beam forming (Step S10 (including Steps S104 through S111)). Meanwhile, the processing in steps other than Step S20 in the flowchart in FIG. 11 is similar to the processing in the corresponding steps in the flowchart in FIG. 6. Thus, description of such similar processing is not provided in the following.

First, coordinate values i and j indicating a position of a measurement point Pij in the ultrasound irradiation area Ax, which can be calculated from the transmission aperture Tx for the initial transmission event, are initialized (set to the respective minimum possible values in the ultrasound irradiation area Ax) (Steps S205 and S206). Then, the reception aperture setter 1042A sets the reception aperture Rx so that the center position of the reception aperture Rx corresponds to a transducer element Xk that is spatially closest to the measurement point Pij (Step S204).

Subsequently, an acoustic line signal is generated for the measurement point Pij (Step S207).

Figure 12:
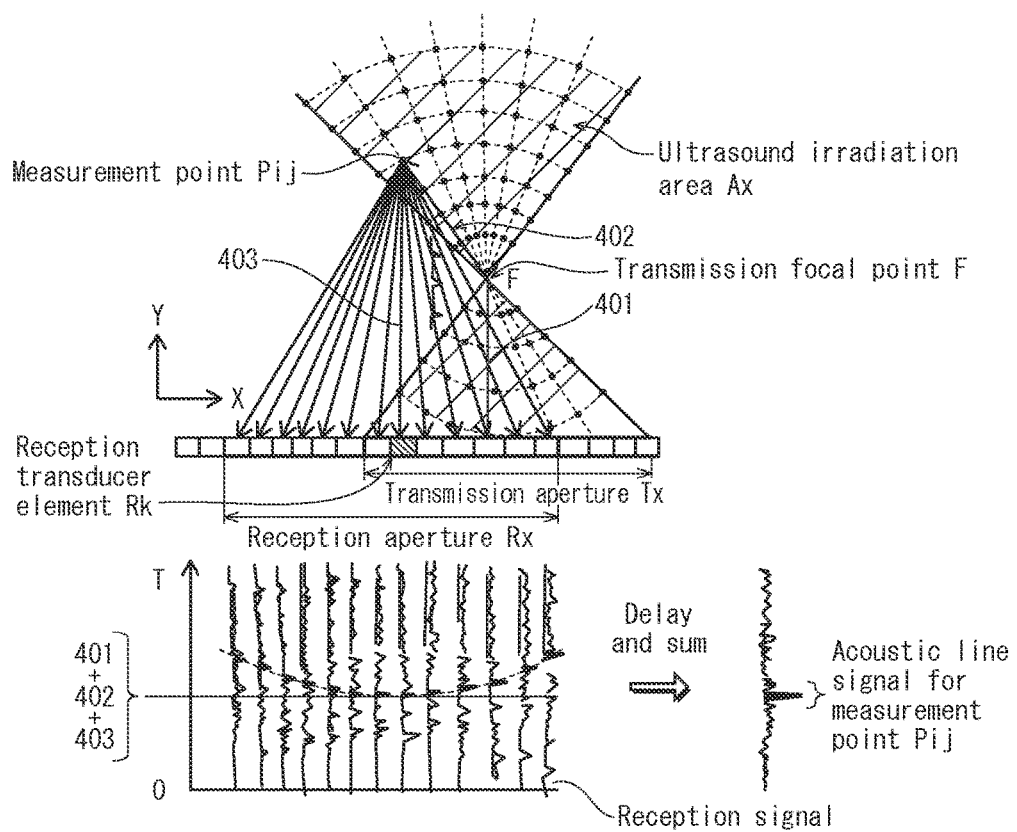
FIG. 12 is a schematic for explaining the operations of the reception beam former 104A for generating an acoustic line signal for a measurement point Pij.

FIG. 12 is a schematic for explaining the operations of the reception beam former 104A for generating the acoustic line signal for the measurement point Pij. The processing in Step S207 is similar to that in Step S107 of FIG. 6 (i.e., Steps S1071 through S1171 in FIG. 7). An acoustic line signal is generated for each measurement point Pij (each illustrated in FIG. 12 as a black dot) within the ultrasound irradiation area Ax by repeating Step S207 while incrementing the coordinate values i and j. Subsequently, a determination is performed of whether or not an acoustic line signal has been generated for every measurement point Pij arranged within the ultrasound irradiation area (Steps S208 and S210). When an acoustic line signal has not yet been generated for one or more measurement points Pij arranged within the ultrasound irradiation area Ax, an acoustic line signal is generated for another measurement point Pij (Step S207) by incrementing the coordinate values i and j (Steps S208 and S210). Meanwhile, when an acoustic line signal has already been generated for each measurement point Pij within the ultrasound irradiation area Ax, processing proceeds to Step S112. At this point, a sub-frame acoustic line signal has already been generated for each measurement point P within the ultrasound irradiation area Ax corresponding to one transmission event, and the sub-frame acoustic line signals have been output to and stored to the data storage 107.

Then, in Step S112, a determination is made of whether there exists in the data storage 107 an acoustic line signal for the same measurement point Pij as the measurement point Pij for which an acoustic line signal has been generated in Step S207. When such an acoustic line signal does exist, the acoustic line signal for the measurement Pij in the data storage 107 has been generated through processing for a different transmission event. When such an acoustic line signal does exist in the data storage 107, the adder 1048 combines the acoustic line signal generated in Step S207 with the corresponding acoustic line signal stored in the data storage 107.

Subsequently, a determination is performed of whether or not sub-frame acoustic line signals have been generated for each transmission event having been performed (Step S113). When sub-frame acoustic line signals have not yet been generated for one or more transmission events, processing returns to Step S205, where coordinate values i and j indicating a position of a measurement point Pij in the ultrasound irradiation area Ax, which can be calculated from the transmission aperture Tx for the subsequent transmission event, are initialized (set to the respective minimum possible values in the ultrasound irradiation area Ax) (Steps S205 and S206), and then setting of the reception aperture Rx is performed (Step S204). Meanwhile, when sub-frame acoustic line signals have been generated for each transmission event having been performed, processing is terminated.

<Effects>

As discussed up to this point, in the ultrasound diagnostic device 100 pertaining to the present embodiment, the reception aperture setter 1042A sets, for each measurement point P, the reception aperture Rx so that the center position of the reception aperture Rx corresponds to a transducer element that is spatially closest to the measurement point P. Accordingly, reception beam forming is performed based on the position of the measurement point P rather than the corresponding transmission event, and by using a reception aperture that is symmetric about the measurement point P (i.e., has the same number of apertures at both sides of the center position thereof in the transducer element array direction). In addition, reception beam forming may be performed by using a reception apodization that has a symmetrical distribution at both sides of the measurement point P in the transducer element array direction. Due to this, the reception aperture (or the reception aperture and apodization weight) for a given measurement point does not change (i.e., the same reception aperture (or the same reception aperture and same apodization weight) is used for the same measurement point) between any transmission events, which involve shifting the transmission focal point F in the transducer element array direction. Thus, delay-and-sum processing for the same measurement point P is always performed by using the same reception aperture (or the same reception aperture and same apodization weight). In addition, in the ultrasound diagnostic device 100A, a weight sequence is set so that the closer a reception transducer element is to the measurement point P, the greater the weight applied to the reception transducer element. Due to this, even taking into account the fact that ultrasound decay increases as propagation distance increases, ultrasound reflected from the measurement point P can be used with high efficiency. Accordingly, the ultrasound diagnostic device 100A achieves both high local spatial resolution and high S/N ratio.

Embodiment 3

The ultrasound diagnostic device 100 pertaining to embodiment 1 includes the reception beam former 104. The reception beam former 104 includes the reception aperture setter 1042, which sets a reception aperture Rx for a given transmission event so that the center position of the reception aperture Rx in the transducer element array direction corresponds to the center position of the transmission aperture Tx for the transmission event. That is, the reception aperture Rx in embodiment 1 can be referred to as a transmission-dependent reception aperture. Meanwhile, the ultrasound diagnostic device 100A pertaining to embodiment 2 includes the reception beam former 104A. The reception beam former 104A includes the reception aperture 1042A, which sets a reception aperture Rx for a given measurement point so that the center position of the reception aperture Rx in the transducer element array direction corresponds to a transducer element that is spatially closest to the measurement point P. That is, the reception aperture Rx in embodiment 2 can be referred to as a measurement point-dependent reception aperture.

Here, note that such beam formers need not be provided and used separately. That is, a modification may be made such that an ultrasound diagnostic device includes both the reception beam former 104 and the reception beam former 104A. With such an ultrasound diagnostic device, both the reception beam former 104 and the reception beam former 104A may be used at the same time, or one of the reception beam former 104 and the reception beam former 104A may be selected and used, based on a predetermined condition or a selection by the operator of the ultrasound diagnostic device. Further, the output from the reception beam former 104 and the output from the reception beam former 104A may be combined (mixed).

Embodiment 3 describes one example of such an ultrasound diagnostic device. In specific, an ultrasound diagnostic device 100B pertaining to embodiment 3, instead of including only one of the reception beam former 104 and the reception beam former 104A, includes an output-selectable reception beam former 104B that includes both the reception beam former 104 and the reception beam former 104A. Other than the output-selectable reception beam former 104B, the constituent elements of the ultrasound diagnostic device 100B have the same structures and configurations as the corresponding constituent elements in embodiment 1. Thus, description of such similar constituent elements is not provided in the following. That is, the ultrasound signal processing device of the ultrasound diagnostic device 100B is constituted of an ultrasound signal processing circuit including, in addition to the output-selectable reception beam former 104B, the multiplexer 102, the transmission beam former 103, and the ultrasound image generator 105.

Figure 13:
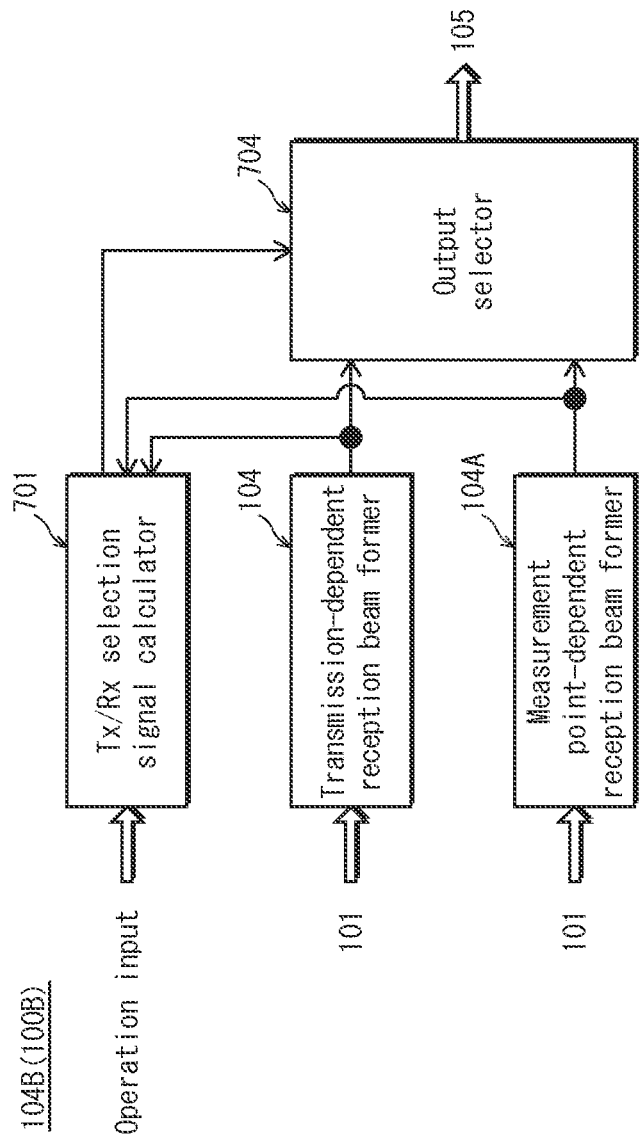
FIG. 13 is a functional block diagram illustrating the structure of a reception beam former 104B of an ultrasound diagnostic device 100B pertaining to embodiment 3.

FIG. 13 is a functional block diagram illustrating the structure of the output-selectable reception beam former 104B of the ultrasound diagnostic device 100B. As illustrated in FIG. 13, the output-selectable reception beam former 104B includes the reception beam former 104, the reception beam former 104A, a Tx/Rx selection signal calculator 701, and an output selector 704. The Tx/Rx selection signal calculator 701 calculates a selection signal indicating output from the reception beam former 104 or output from the reception beam former 104A, based on output from at least one of the reception beam former 104 and the reception beam former 104A. The output selector 704 selects the output from the reception beam former 104 or the output from the reception beam former 104A based on the selection signal, and outputs the selected output.

The Tx/Rx selection signal calculator 701 receives, as input, an acoustic line signal output from the reception beam former 104 (referred to in the following as a first acoustic line signal) and/or an acoustic line signal output from the reception beam former 104A (referred to in the following as a second acoustic line signal). Further, the Tx/Rx selection signal calculator 701 calculates a selection signal based on, for example, which of the first and second acoustic line signals indicates a greater value (may be a luminance value), and outputs the selection signal so calculated to the output selector 704. Here, the selection signal indicates one of the first acoustic line signal and the second acoustic line signal. Further, here, each of the first acoustic line signal and the second acoustic line signal, respectively output from the reception beam former 104 and the reception beam former 104A and input to the Tx/Rx selection signal calculator 701, is a delay-and-sum acoustic line signal for the same measurement point P within the ultrasound irradiation area Ax. As already discussed above, the ultrasound irradiation area Ax is an area inside the subject and has an hourglass shape. Further, as already discussed above, each of the reception beam former 104 and the reception beam former 104A generates the acoustic line signal for the measurement point P according to the synthetic aperture method. The output selector 704 receives the selection signal from the Tx/Rx selection signal calculator 701 as input. Further, the output selector 704 outputs, to the ultrasound image generator 105, one of the first acoustic line signal and the second acoustic line signal, whichever one is indicated by the selection signal. Here, note that the Tx/Rx selection signal calculator 701 may alternatively receive as input, from at least one of the reception beam former 104 and the reception beam former 104A, reception signals yielded through A/D conversion of electric signals that are based on reflected ultrasound acquired by a plurality of transducer elements of the probe 101, for example. Further, it is preferable that the selection of the signal to be output from the output selector 704 be performed frame by frame. Nevertheless, the selection of the signal to be output from the output selector 704 may be performed for each measurement point or for each transmission event.

The following describes another example of the selection related to the output from the reception beam former 104 and the output from the reception beam former 104A. In specific, the following describes an example of how the Tx/Rx selection signal calculator 701 and the output selector 704 may operate.

In typical biopsy, a sample of tissue, fluid, etc., is removed with a puncture needle inserted into a living subject, and the sample is examined. Here, the insertion of the puncture needle into the living subject is performed while checking the position of the puncture needle. Further, there are cases where the puncture needle is attached to an ultrasound probe having an attachment, a guide, or the like for attaching the puncture needle, and the insertion of the puncture needle is performed while checking the position of the puncture needle in ultrasound images. In view of such cases, a configuration may be made, for example, such that the Tx/Rx selection signal calculator 701 determines whether or not a puncture needle is being inserted into the subject based on the first acoustic line signal or the second acoustic line signal, and when determining that the puncture needle is present in the subject, the Tx/Rx selection signal calculator 701 outputs a selection signal indicating the first acoustic line signal (i.e., the reception beam former 104). In this configuration, the Tx/Rx selection signal calculator 701 determines that the puncture needle is present when the acquired one of the first acoustic line signal and the second acoustic line signal indicates, with high luminance, a linear reflection area that is at least partially exposed to the outside from the body surface of the subject.

Here, it should be noted that ultrasound reflection from a puncture needle indicates a strong influence of specular reflection, whereas ultrasound reflection (echo images) from a tissue of a living subject typically indicates a strong influence of diffuse reflection. Due to this, a puncture needle generates strong ultrasound reflection in a specific direction that is dependent upon the angle at which the puncture needle is inserted into the living subject and the position of the puncture needle relative to the probe. Thus, in order to detect ultrasound reflected by a puncture needle, it is essential to receive ultrasound reflection from the specific direction. In view of this, the reception beam former 104 pertaining to the present disclosure is suitable for receiving the ultrasound reflection from the specific direction, due to using a group of reception apertures covering a vast measurement area according to the synthetic aperture method. That is, the reception beam former 104 is suitable for the detection of ultrasound reflection from a puncture needle.

Note that the above-described configuration of utilizing the output from the reception beam former 104 rather than the output from the reception beam former 104A is similarly applicable to cases where any object causing specular reflection is being inserted into any subject.

Further, the Tx/Rx selection signal calculator 701 may select one of the first acoustic line signal and the second acoustic line signal based on input performed by the operator or based on a predetermined condition. Here, the input performed by the operator may be input for selecting one of the first acoustic line signal and the second acoustic line signal. Alternatively, the input performed by the operator may be input that is an instruction for an operation other than the selection of one of the first acoustic line signal and the second acoustic line signal. For example, input by the operator for an operation other than the selection of one of the first acoustic line signal and the second acoustic line signal may be input for selecting a puncture needle mode to be used in puncture needle insertion. The puncture needle mode is a mode where images including both the subject and the puncture needle are created, which allows the operator to grasp the position of the puncture needle with respect to the subject. A further configuration may be made, for example, such that in the puncture needle mode, a puncture needle tip is displayed with emphasis. For example, the operator may select the puncture needle mode via any input unit (e.g., a keyboard) connected to the ultrasound diagnostic device or any input unit (e.g., a key) provided to the ultrasound diagnostic device. Alternatively, the ultrasound diagnostic device may select the puncture needle mode when a predetermined ultrasound probe having been registered in advance is connected thereto.

Further, when the output-selectable reception beam former 104B is preset to output a predetermined one of the output from the reception beam former 104 and the output from the reception beam former 104A (i.e., when the Tx/Rx selection signal calculator 701 is preset to output the predetermined one), the output selector 704 outputs the predetermined one of the output from the reception beam former 104 and the output from the reception beam former 104A as-is.

<Modification 1>

The following describes modification 1 (modification of embodiment 3). An ultrasound diagnostic device 100C pertaining to the present modification includes an output-mixable reception beam former 104C, in place of the output-selectable beam former 104B pertaining to embodiment 3. Other than the output-mixable reception beam former 104C, the constituent elements of the ultrasound diagnostic device 100C have the same structures and configurations as the corresponding constituent elements in embodiment 1. Thus, description of such similar constituent elements is not provided in the following. That is, the ultrasound signal processing device of the ultrasound diagnostic device 100C is constituted of an ultrasound signal processing circuit including, in addition to the output-mixable reception beam former 104C, the multiplexer 102, the transmission beam former 103, and the ultrasound image generator 105.

Figure 14:
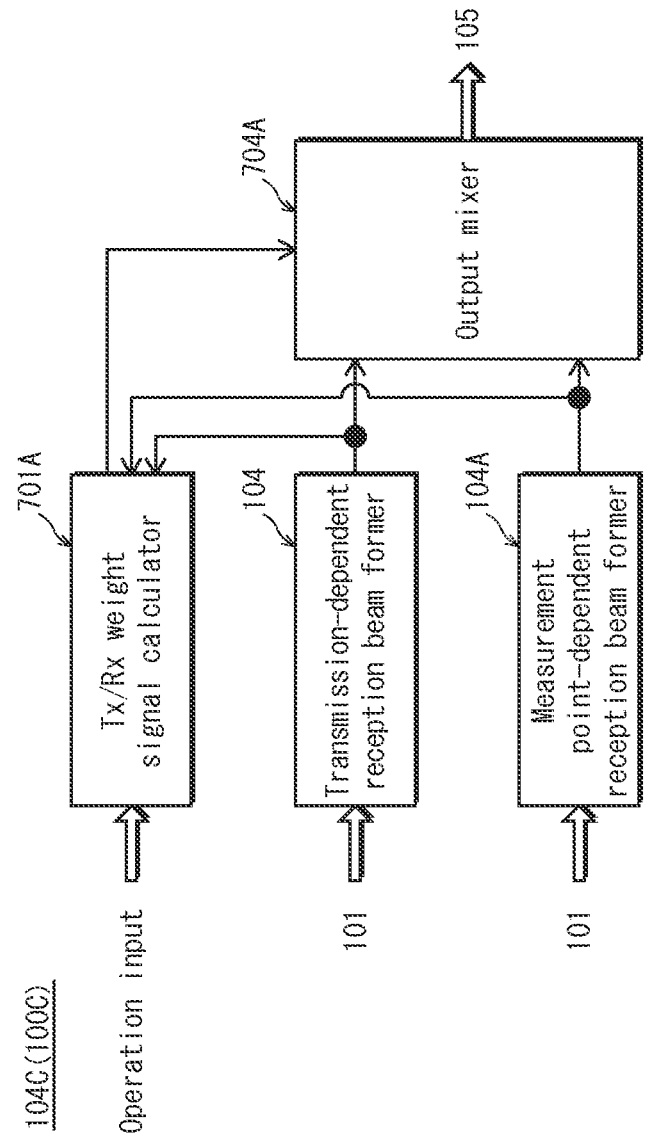
FIG. 14 is a functional block diagram illustrating the structure of a reception beam former 104C of an ultrasound diagnostic device 100C pertaining to modification 1.

FIG. 14 is a functional block diagram illustrating the structure of the output-mixable reception beam former 104C of the ultrasound diagnostic device 100C. As illustrated in FIG. 14, the output-mixable reception beam former 104C includes the reception beam former 104, the reception beam former 104A, a Tx/Rx weight signal calculator 701A, and an output mixer 704A. The Tx/Rx weight signal calculator 701A, based on the output from the reception beam former 104 and the output from the reception beam former 104A, calculates a weight signal indicating weights to be applied to the output from the reception beam former 104 and the output from the reception beam former 104A. The output mixer 704A multiplies the output from the reception beam former 104 and the output from the reception beam former 104A by the respective weights indicated by the weight signal, sums the weight-applied output from the reception beam former 104 and the weight-applied output from the reception beam former 104A, and outputs the calculated sum.

In specific, the Tx/Rx weight signal calculator 701A receives, as input, an acoustic line signal output from the reception beam former 104 (referred to in the following as a first acoustic line signal) and an acoustic line signal output from the reception beam former 104A (referred to in the following as a second acoustic line signal). Further, the Tx/Rx weighting signal calculator 701A calculates a weight signal based on, for example, the ratio between the average value (may be a luminance-related value) of the first acoustic line signal and the average value of the second acoustic line signal, and outputs the weight signal. The weight signal indicates the ratio at which the first and second acoustic line signals are to be mixed. The output mixer 704A receives the weight signal output from the Tx/Rx weighting signal calculator 701A as input. Further, the output mixer 704A multiplies the first acoustic line signal and the second acoustic line signal by the respective weights indicated by the weight signal, sums the weight-applied first acoustic line signal and the weight-applied second acoustic line signal, and outputs the result of the calculation to the ultrasound image generator 105. Here, note that the Tx/Rx weight signal calculator 701 may alternatively receive as input, from each of the reception beam former 104 and the reception beam former 104A, reception signals yielded through A/D conversion of electric signals that are based on reflected ultrasound acquired by a plurality of transducer elements of the probe 101, for example. Further, it is preferable that the changing of mixing ratio of the signal output from the output mixer 704A be performed frame by frame. Nevertheless, the changing of mixing ratio of the signal output from the output mixer 704A may be performed for each measurement point or for each transmission event.

Further, the Tx/Rx weight signal calculator 701A may mix the first acoustic line signal and the second acoustic line signal based on input performed by the operator or based on a predetermined condition. For example, when a predetermined mixing ratio for mixing the output from the reception beam former 104 and the output from the reception beam former 104A is set (e.g., when a mixing ratio of 0.6:0.4 is set) to the Tx/Rx weight signal calculator 701A, the output mixer 704A multiples the output from the reception beam former 104 and the output from the reception beam former 104A by the respective weights indicated by the predetermined mixing ratio, sums the weight-applied outputs, and outputs the sum as the output of the output-mixable reception beam former 104C. Here, the operator may specify the mixing ratio for mixing the output from the reception beam former 104 and the output from the reception beam former 104A. Further, the operator may cause only one of the two to be output.

<Effects>

The output-selectable reception beam former 104B in the ultrasound diagnostic device 100B (embodiment 3) and the output-mixable reception beam former 104C in the ultrasound diagnostic device 100C (modification 1) are configured to set the reception aperture Rx adaptively and appropriately depending upon examination-target part characteristics. Thus, embodiment 3 and modification 1, while ensuring adaptiveness to examination-target part characteristics, achieve both high spatial resolution at local areas in images and uniform spatial resolution over wide areas in images.

In specific, the ultrasound diagnostic device 100 includes the transmission-dependent reception beam former 104. The reception beam former 104 utilizes a large number of reception apertures, and thereby is capable of utilizing ultrasound reflected from the measurement point P over a wide angular range. Thus, the ultrasound diagnostic device 100 creates an image reflecting the utilization of reflected ultrasound from a wide angular range, and thus is capable of improving the spatial resolution of the image. Thus, the ultrasound diagnostic device 100, by utilizing a group of virtual reception apertures covering a vast measurement area, is capable of achieving uniform spatial resolution over a wide measurement area. Thus, the ultrasound diagnostic device 100 is effective for examination of an examination-target part such as an internal organ reflecting ultrasound at uniform intensity at different areas thereof, or in other words, an examination-target part that does not reflect ultrasound at extremely different intensities at different areas thereof. Using a large number of reception apertures Rx results in uniform spatial resolution over a wide measurement area. Due to this, an image created by the ultrasound diagnostic device 100 has high quality over a wide measurement area, and thus, is relatively suitable for an examination such as where a specific part of the subject that is affected by some type of disorder (a specific examination-target part) has not yet been specified and the examination is being performed to specify a specific examination-target part. Meanwhile, it should be noted that depending upon examination-target part characteristics, an image created by the ultrasound diagnostic device 100 may include signals from areas other than the measurement point P, which may be referred to as noise.

Meanwhile, the ultrasound diagnostic device 100A includes the measurement point-dependent reception beam former 104A. With the reception beam former 104A, the reception aperture Rx for one measurement point P is always located at the same position in the transducer element array direction, irrespective of transmission events. Due to this, for the same measurement point P, the ultrasound diagnostic device 100A performs reception beam forming by using a smaller number of reception apertures Rx than the ultrasound diagnostic device 100. Accordingly, the ultrasound diagnostic device 100A achieves both high local spatial resolution and high S/N ratio. For example, the ultrasound diagnostic device 100A is effective when used for examination of an examination-target part including a specific examination-target area that has already been specified, such as a polyp, whose ultrasound reflection indicates high local intensity. Using a small number of reception apertures Rx yields a high quality image having high local spatial resolution and high S/N ratio. Meanwhile it should be noted that with the ultrasound diagnostic device 100A, when the reception aperture Rx is far from the transmission focal point F, the total intensity of reception signals acquired by the reception apertures in the reception aperture Rx, as a result of reflected ultrasound reception, is smaller compared to when the reception aperture Rx is close to the transmission focal point F. Accordingly, depending upon examination-target part characteristics, the reception sensitivity and the S/N ratio achieved by the ultrasound diagnostic device 100A may be low.

In view of this, the ultrasound diagnostic device 100B pertaining to embodiment 3 and the ultrasound diagnostic device 100C pertaining to modification 1 include reception beam formers enabling setting the reception aperture Rx appropriately depending upon examination-target part characteristics. The setting of the reception aperture may be performed through selection by the operator, or based on a characteristic of reception signals. Thus, embodiment 3 and modification 1, while ensuring adaptiveness to examination-target part characteristics, achieve both high spatial resolution at local areas in images and uniform spatial resolution over wide areas in images. This results in the generation of high quality ultrasound images having higher resolution and less noise over the entirety of an ultrasound irradiation area than conventional technology.

<Modification 2>

The following describes modification 2. An ultrasound diagnostic device pertaining to the present modification includes the output-mixable reception beam former 104C pertaining to modification 1, modified to receive as input and use a reception signal yielded through A/D conversion of electric signals that are based on reflected ultrasound acquired by the probe 101. In the modified output-mixable reception beam former 104C pertaining to the present modification, the Tx/Rx weight signal calculator 701A extracts a characteristic of the reception signal, and adaptively changes the weight signal based on the characteristic so extracted.

Figure 15:
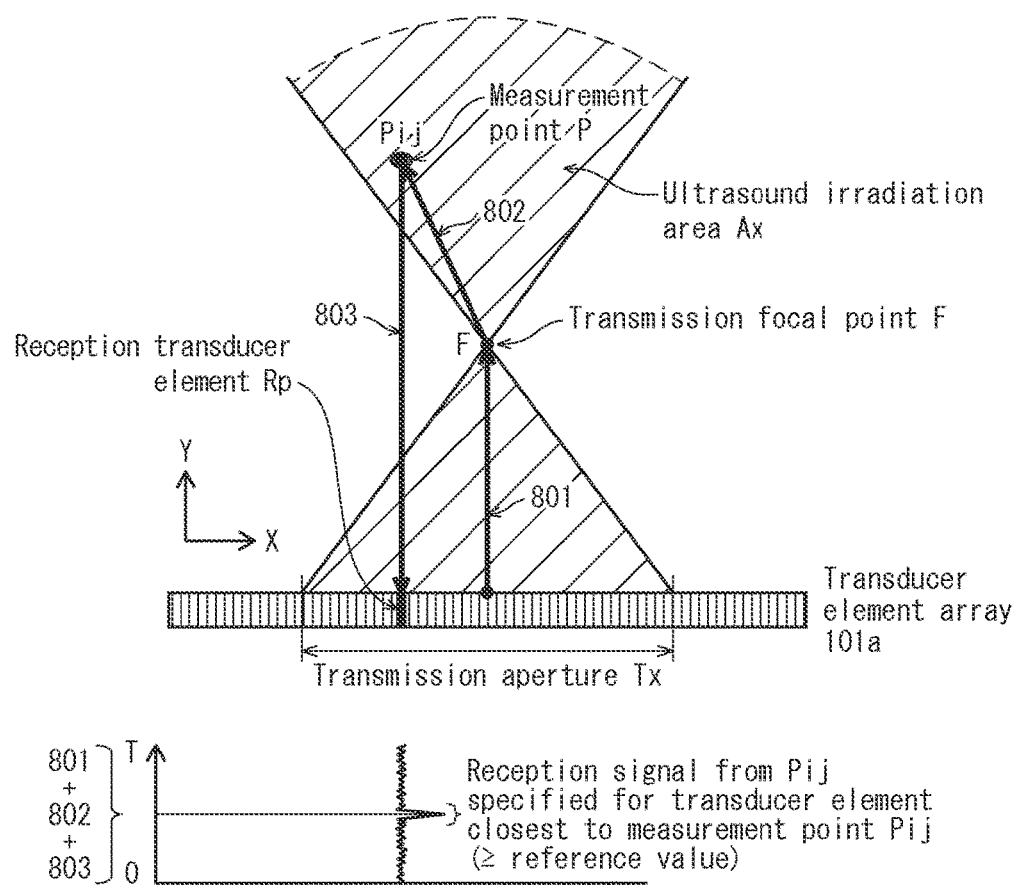
FIG. 15 is a schematic for explaining a signal input to a Tx/Rx weight signal calculator 701A of a reception beam former of an ultrasound diagnostic device pertaining to modification 2.
Figure 16:
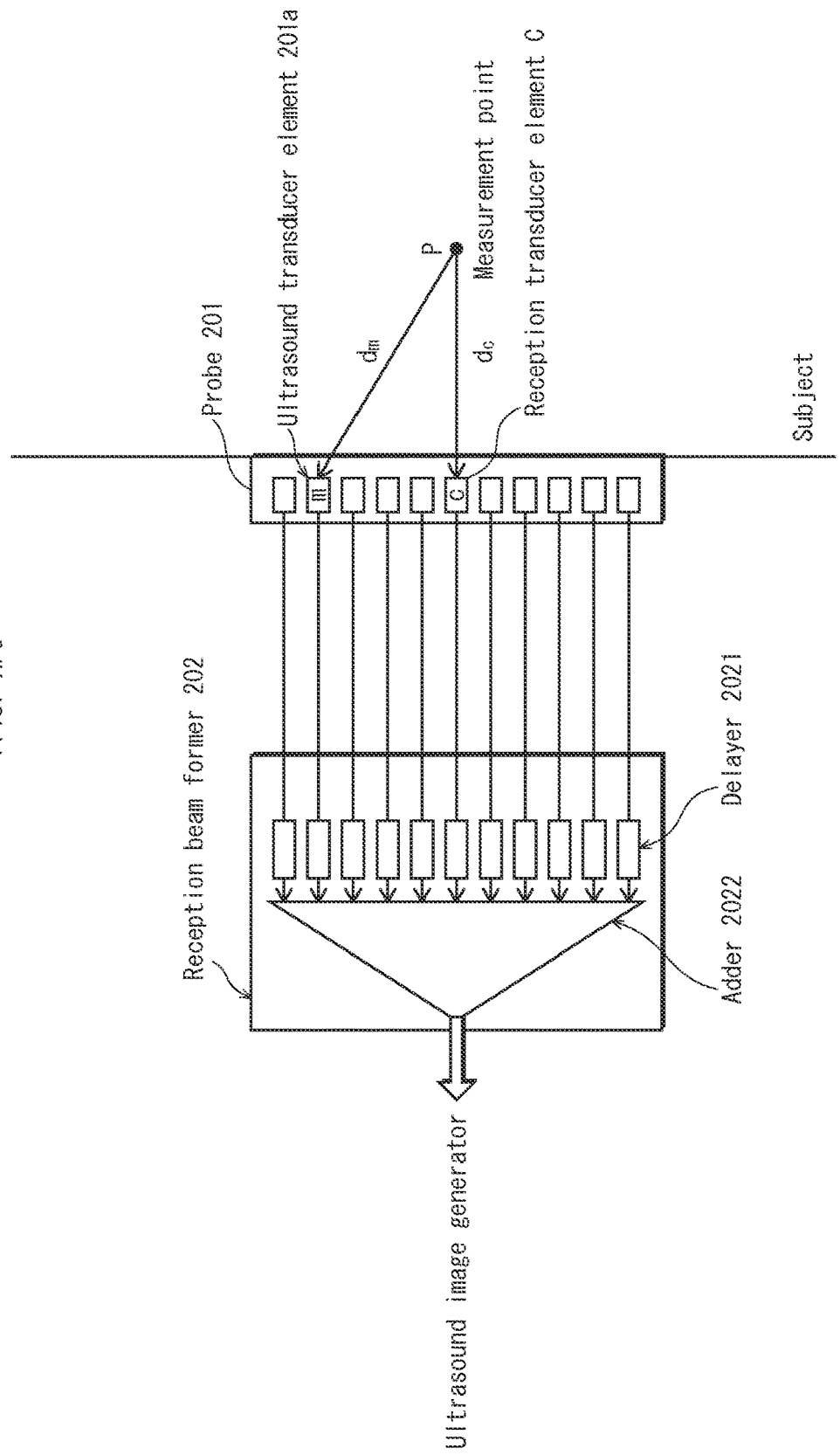
FIG. 16 is a schematic for explaining the operations of a reception beam former 202 of a conventional ultrasound signal processing device.

FIG. 15 is a schematic for explaining one example of the reception signal input to the Tx/Rx weight signal calculator 701A of the modified output-mixable reception beam former 104C of the ultrasound diagnostic device pertaining to modification 2. The reception signal illustrated in FIG. 15 is based on a reflection of ultrasound that is transmitted from the transmission aperture Tx, is reflected at a measurement point Pij arranged within the ultrasound irradiation area Ax, and arrives at a reception transducer element Rp included in the reception aperture Rx. Here, the reception transducer element Rp corresponds to a transducer element closest to the measurement point Pij. FIG. 15 illustrates propagation paths 801, 802, and 803. The reception signal illustrated in FIG. 15 has a value based on the total of propagation paths 801, 802, and 803. Here, the present inventor has clarified, through research and consideration, that there is a strong correlation between the reception signal for the reception transducer element Rp and a signal yielded by performing reception beam forming with respect to the reception signal for the reception transducer element Rp. For example, in many cases, when the reception signal for the reception transducer element Rp, which is specified by performing delaying based on the total of the propagation paths 801, 802, and 803, has a great value, the signal yielded by performing reception beam forming with respect to this reception signal for the reception transducer element Rp also has a great value. Thus, the control by the Tx/Rx weight calculator 701A can be simplified by taking advantage of this characteristic.

As discussed above, in modification 1, both the transmission-dependent reception beam former 104 and the measurement point-dependent reception beam former 104A are caused to operate, and the Tx/Rx weight calculator 701A calculates weights based on the delay-and-sum output from each of the reception beam former 104 and the reception beam former 104A. Thus, modification 1 requires causing two reception beam formers to operate, which requires the ultrasound diagnostic device to have high computation capacity. In view of this, the present modification achieves a reduction in computation load, by making a determination based on the value of the reception signal for the reception transducer element Rp, which is yielded by performing delaying based on the total of the propagation paths 801, 802, and 803 and which is a signal before delay-and-sum processing, and calculating a weight based on the determination.

For example, when the reception signal for the reception transducer element Rp has a value greater than a predetermined threshold A, the modified output-mixable reception beam former 104C outputs what is output from the measurement point-dependent reception beam former 104A as-is. Meanwhile, when the reception signal for the reception transducer element Rp has a value smaller than a predetermined threshold B, the modified output-mixable reception beam former 104C outputs what is output from the transmission-dependent reception beam former 104 as-is. Further, when the reception signal for the reception transducer element Rp has a value between the thresholds A and B, a predetermined maxing ratio is calculated based on a predetermined method, and the output mixer 704A mixes the output from the reception beam formers 104 and 104A based on the predetermined mixing ratio. Further, the output mixer 704A outputs the result of the mixing as the output of the modified output-mixable reception beam former 104C.

In the above, when setting the same value to both threshold A and threshold B, the Tx/Rx weight calculator 701A functions as a switch, and the output mixer 704 outputs, as the output of the modified output-mixable reception beam former 104C, a selected one of the output from the reception beam former 104 and the output from the reception beam former 104. This results in the modified output-mixable reception beam former 104C functioning in the same way as the output-selectable reception beam former 104B pertaining to embodiment 3.

Using the modified output-mixable reception beam former described above results in simplified processing with relatively low computation load. Thus, the present modification provides a simple circuit structure that enables setting a suitable reception beam forming method in accordance with a selection by the operator, or a characteristic of a reception signal. This results in the generation of high quality ultrasound images having higher resolution and less noise over the entirety of an ultrasound irradiation area than conventional technology.

<Other Modifications>

Up to this point, the technology pertaining to the present disclosure has been described based on specific embodiments and modifications thereof. However, the embodiments and modifications described above are non-limiting examples of application of the technology pertaining to the present disclosure, and thus, the technology pertaining to the present disclosure shall be construed to encompass the following exemplar modifications.

For example, the technology pertaining to the present disclosure may be implemented by using a computer system including a memory storing a computer program and a microprocessor operating based on the computer program. For example, the computer system may store a computer program of a diagnosis method of an ultrasound diagnostic device pertaining to the technology of the present disclosure, and the computer system may operate in accordance with the computer program or may provide instructions in accordance with the computer program to various components connected thereto.

Further, the technology pertaining to the present disclosure may be implemented by implementing a part of or the entirety of an ultrasound diagnostic device described above, or a part of or an entirety of an beam former described above by using a computer system including a microprocessor, a recording medium such as a ROM or a RAM, and a hard disk unit. In this implementation, a computer program achieving the same operations as a device described above is stored to the RAM or the hard disk unit. Further, in this implementation, various devices achieve their functions by the microprocessor operating in accordance with the computer program.

Further, the technology pertaining to the present disclosure may be implemented by implementing some or all constituent elements included in a device described above by using one system LSI (large scale integration). A system LSI is an ultra-multifunctional LSI manufactured by integrating multiple components onto one chip. Specifically, a system LSI is a computer system including a microprocessor, a ROM, a RAM, and the like. Further, each constituent element may be separately implemented by using one chip, or some or all constituent elements may be implemented by using one chip. Note that LSIs are referred to by using different names, depending upon the level of integration achieved thereby. Such names include IC, system LSI, super LSI, and ultra LSI. In this implementation, a computer program achieving the same operations as any device described above is stored to the RAM. Further, in this implementation, the system LSI achieves its functions by the microprocessor operating in accordance with the computer program. For example, the technology pertaining to the present disclosure encompasses a form of implementation where an LSI stores a beam forming method pertaining to the present disclosure as a program, the LSI is inserted into a computer, and the computer executes the program (i.e., the beam forming method pertaining to the present disclosure).

Note that integration of circuits may be achieved by a dedicated circuit or a general purpose processor, in addition to being achievable by using an LSI as discussed above. Further, a Field Programmable Gate Array (FPGA), which is programmable after manufacturing, or a reconfigurable processor, which allows reconfiguration of the connection and setting of circuit cells inside the LSI, may be used.

Furthermore, if technology for circuit integration that replaces LSIs emerges, owing to advances in semiconductor technology or to another derivative technology, the integration of functional blocks may naturally be accomplished using such technology.

Further, some or all functions of an ultrasound diagnostic device discussed in the embodiments may be implemented by a processor such as a CPU executing a program. Further, the technology pertaining to the present disclosure may be implemented by using a non-transitory computer-readable recording medium having recorded thereon a program causing execution of a diagnostic method and a beam forming method of an ultrasound diagnostic device. Further, execution of the program by another independent computer system may be achieved by transferring the program by recording the program or a signal onto a recording medium. Naturally, the program may be distributed via means of transmission media such as the internet.

Each of the ultrasound diagnostic devices pertaining to the embodiments includes the data storage, which is a recording device. However, the recording device need not be included in the ultrasound diagnostic devices, and may be implemented by using a semiconductor memory, a hard disk drive, an optical disk drive, a magnetic storage device, or the like connected to the ultrasound diagnostic devices from the outside.

Further, the functional blocks illustrated in the block diagrams are mere examples of possible functional blocks. That is, a plurality of functional blocks illustrated in the block diagrams may be combined to form one functional block, a given functional block illustrated in the block diagrams may be divided into a plurality of functional blocks, and a function of a given functional block illustrated in the block diagrams may be transferred to another functional block. Further, with regards to multiple functional blocks having similar functions, such functional blocks may be implemented by one piece of hardware or software executing such functions in parallel or by applying time division.

Further, the above-described order in which steps of processing are executed is a non-limiting example among multiple possible orders that is used for the sole sake of providing specific description of the technology pertaining to the present disclosure. Further, some of the steps of processing described above may be executed simultaneously (in parallel).

Further, in the embodiments, description is provided that the ultrasound diagnostic devices may have a probe and a display attached thereto. However, the ultrasound diagnostic devices may include a probe and a display therein.

Further, in the embodiments, the probe includes a plurality of piezoelectric transducer elements forming a line in one direction. However, the probe may have a different structure. For example, the probe may include a plurality of piezoelectric transducer elements disposed two-dimensionally. Alternatively, the probe may include a plurality of swingable transducer elements (i.e., transducer elements that can be caused to swing by mechanical means) forming a line in one direction, which enables acquisition of three-dimensional tomographic images. Further, probes of different types may be selected and used depending upon the examination to be performed. For example, when using a probe including piezoelectric transducer elements disposed two-dimensionally, supplying different piezoelectric transducer elements with voltages at different timings or with voltages with different values achieves controlling the position, the direction, etc., of the ultrasound beam to be transmitted.

Further, the probe may be provided with some of the functions of the transmission beam former/reception beam former. For example, the probe may be capable of generating a transmission electric signal based on a control signal that the transmission beam former/reception beam former outputs to cause generation of a transmission electric signal, and of converting the transmission electronic signal into ultrasound. In addition, the probe may be capable of converting reflected ultrasound into a reception electric signal, and of generating a reception signal based on the reception electric signal.

Further, at least some of the functions of the ultrasound diagnostic devices pertaining to the embodiments and the modifications may be combined with functions of other ones of the ultrasound diagnostic devices pertaining to the embodiments and the modifications. Further, the values used above are non-limiting examples used for the sole sake of providing specific description of the technology pertaining to the present disclosure, and may be replaced with other values.

Further, the technology pertaining to the present disclosure should be construed as encompassing various modifications that a skilled artisan would arrive at based on the embodiments describe above.

CONCLUSION

As discussed up to this point, one aspect of the present disclosure is an ultrasound signal processing device 150 that causes an ultrasound probe 101 having a plurality of transducer elements to transmit ultrasound towards a subject to acquire ultrasound reflected from the inside of the subject, generates a reception signal from the reflected ultrasound, and generates an acoustic line signal from the reception signal. The ultrasound signal processing device includes: an ultrasound signal processing circuit 151 that functions as: a transmitter 1031 performing an ultrasound transmission session of causing a transmission transducer element array composed of all or some of the transducer elements to transmit ultrasound; a receiver 1041 generating a plurality of reception signal sequences, one for each of the transducer elements, each of the reception signal sequences generated based on reflected ultrasound that a corresponding one of the transducer elements receives in response to the transmission of the ultrasound; a first reception aperture setter 1042 designating a first reception transducer element array composed of some of the transducer elements and having a center position corresponding to a center position of the transmission transducer element array; a transmission time calculator 1043 performing, for each of a plurality of predetermined measurement points arranged within an assumed area of reach of the ultrasound inside the subject, a calculation of transmission time that is a time period from transmission of the ultrasound until arrival of the ultrasound at the measurement point; a first reception time calculator 1044 performing, for each of the measurement points, a calculation of reception time for each first reception transducer element in the reception transducer element array, the reception time being a time period from reflection of the ultrasound at the measurement point until arrival of the ultrasound at the first reception transducer element; a first delay amount calculator 1045 performing, for each of the measurement points, (i) a calculation of total propagation time for each first reception transducer element, the total propagation time being a sum of the transmission time and the reception time for the first reception transducer element, and (ii) a calculation of a delay amount for each first reception transducer element based on the total propagation time for the first reception transducer element; a first delay processor 1046 performing, for each of the measurement points, a specification of a reception signal value for each first reception transducer element, the specified reception signal value being a reception signal value corresponding to the delay amount for the first reception transducer element, from among reception signal values composing one of the reception signal sequences that corresponds to the first reception transducer element; and a first adder 1048 generating a first acoustic line signal for each of the measurement points, based on the specified reception signal values for the first reception transducer elements specified with respect to the measurement point. The first adder 1048 may calculate a sum of the specified reception signal values for the first reception transducer elements.

This structure achieves generation of high quality ultrasound images having higher resolution and less noise over the entirety of an ultrasound irradiation area than conventional technology.

In the ultrasound signal processing device pertaining to one aspect of the present disclosure, the ultrasound signal processing circuit may also function as: a first weight calculator 1047 calculating a weight sequence for the first reception transducer element array, the weight sequence including the greatest weight for a first reception transducer element at the center position of the first reception transducer element array, and the first adder 1048 may generate the first acoustic signal line for each of the measurement points by, for each first reception transducer element, multiplying the specified reception signal value for the first reception transducer element specified with respect to the measurement point by a weight included in the weight sequence that corresponds to the first reception transducer element, and by summing products yielded by performing the multiplication for each first reception transducer element.

This achieves performing delay-and-sum processing by using a different reception aperture for each transmission event, thereby achieving the effects of reception processing using a group of reception apertures covering a vast measurement area. Accordingly, this achieves uniform spatial resolution over wide areas in images.

In the ultrasound signal processing device pertaining to one aspect of the present disclosure, the ultrasound signal processing circuit may also function as: a second reception aperture setter 1042A performing, for each of the measurement points, a designation of a second reception transducer element array composed of some of the transducer elements and having a center position corresponding to one of the transducer elements that is closest to the measurement point; a second reception time calculator 1044 performing, for each of the measurement points, a calculation of reception time for each second reception transducer element in the second reception transducer element array, the reception time being a time period from reflection of the ultrasound at the measurement point until arrival of the ultrasound at the second reception transducer element; a second delay amount calculator 1045 performing, for each of the measurement points, (i) a calculation of total propagation time for each second reception transducer element, the total propagation time being a sum of the transmission time and the reception time for the second reception transducer element, and (ii) a calculation of a delay amount for each second reception transducer element based on the total propagation time for the second reception transducer element; a second delay processor 1046 performing, for each of the measurement points, a specification of a reception signal value for each second reception transducer element, the specified reception signal value being a reception signal value corresponding to the delay amount for the second reception transducer element, from among reception signal values composing one of the reception signal sequences that corresponds to the second reception transducer element; and a second adder 1048 generating a second acoustic line signal for each of the measurement points, based on the specified reception signal values for the second reception transducer elements specified with respect to the measurement point. The second adder 1048 may calculate a sum of the specified reception signal values for the second reception transducer elements.

This achieves using the same reception aperture for a given measurement point (i.e., the same reception aperture is used for the same measurement point) irrespective of transmission events, which involve shifting the transmission focal point F in the transducer element array direction. Thus, delay-and-sum processing for the same measurement point P is always performed by using the same reception aperture.

In the ultrasound signal processing device pertaining to one aspect of the present disclosure, the ultrasound signal processing circuit may also function as: a second weight calculator 1047 calculating a weight sequence for the second reception transducer element array, the weight sequence including the greatest weight for a second reception transducer element at the center position of the second reception transducer element array, and the second adder 1048 generates the second acoustic signal line for each of the measurement points by, for each second reception transducer element, multiplying the specified reception signal value for the second reception transducer element specified with respect to the measurement point by a weight included in the weight sequence that corresponds to the second reception transducer element, and by summing products yielded by performing the multiplication for each second reception transducer element.

This achieves setting a weight sequence so that that the closer a reception transducer element is to the measurement point P, the greater the weight applied to the reception transducer element. Due to this, even taking into account the fact that ultrasound decay increases as propagation distance increases, ultrasound reflected from the measurement point P can be used with high efficiency. Accordingly, this achieves both high local spatial resolution and high S/N ratio.

In the ultrasound signal processing device pertaining to one aspect of the present disclosure, the ultrasound signal processing circuit may also function as: a Tx/Rx selection signal calculator 701 selecting one of the first acoustic line signal and the second acoustic line signal; and an output selector 704 that outputs one of the first acoustic line signal and the second acoustic line signal in accordance with the result of the selection by the Tx/Rx selection signal calculator. The Tx/Rx selection signal calculator 701 may perform the selection based on input performed by an operator of the ultrasound signal processing device or based on a predetermined condition. The Tx/Rx selection signal calculator 701 may perform the selection based on a characteristic of the plurality of reception signal sequences. The Tx/Rx selection signal calculator 701 may determine whether or not a puncture needle is being used with respect to the subject and may select the first acoustic line signal when determining that a puncture needle is being used with respect to the subject. The Tx/Rx selection signal calculator 701, when detecting an object causing specular reflection based on the plurality of reception signal sequences, may determine that a puncture needle is being used with respect to the subject and selects the first acoustic line signal. The Tx/Rx selection signal calculator 701 may perform the selection based on at least one of the first acoustic line signal and the second acoustic line signal. In addition, the ultrasound signal processing circuit may also function as: a Tx/Rx weight calculator 701A calculating a weight for the first acoustic line signal and a weight for the second acoustic line signal; and an output mixer 704A performing a calculation of multiplying each of the first acoustic line signal and the second acoustic line signal by a corresponding weight and summing the products yielded by performing the multiplication with respect to each of the first acoustic line signal and the second acoustic line signal, and outputting a result of the calculation. The Tx/Rx weight calculator 701A may perform, for each of the measurement points, a calculation of the weight corresponding to the first acoustic line signal and the weight corresponding to the second acoustic line signal based on input performed by an operator of the ultrasound signal processing device or based on a predetermined condition. The Tx/Rx weight calculator 701A may calculate the weight corresponding to the first acoustic line signal and the weight corresponding to the second acoustic line signal based on a characteristic of the plurality of reception signal sequences. The Tx/Rx weight calculator 701A may calculate the weight corresponding to the first acoustic line signal and the weight corresponding to the second acoustic line signal based on the first acoustic line signal and the second acoustic line signal.

This achieves a reception beam former configured to set the reception aperture Rx appropriately in accordance with examination-target part characteristics, through selection by the operator, or based on a characteristic of reception signals. Thus, in addition to adaptiveness to examination-target part characteristics being achieved, both high spatial resolution at local areas in images and uniform spatial resolution over wide areas in images are also achieved. This results in the generation of high quality ultrasound images having higher resolution and less noise over the entirety of an ultrasound irradiation area than conventional technology.

In the ultrasound signal processing device pertaining to one aspect of the present disclosure, the characteristic of the plurality of reception signal sequences may be calculated based on the reception signal value for a first reception transducer element with the smallest delay amount in the first reception transducer element array and the reception signal value for a second reception transducer element with the smallest delay amount in the second transducer element array.

This achieves using employing simplified processing with relatively low computation load, and thereby achieves a simple circuit structure that enables setting a suitable reception beam forming method in accordance with a selection by the operator, or a characteristic of a reception signal.

In the ultrasound signal processing device pertaining to one aspect of the present disclosure, the transmission transducer element array may be composed of only some of the transducer elements of the ultrasound probe, the transmitter 1031 may perform a plurality of ultrasound transmission sessions while changing the transducer elements of the ultrasound probe included in transmission transducer element array each time, and the first adder 1048 may generate the first acoustic line signal for each of the measurement points by synthesizing a plurality of first acoustic line signals for the measurement point, each of which acquired based on one of the ultrasound transmission sessions.

In the ultrasound signal processing device pertaining to one aspect of the present disclosure, the transmission transducer element array may be composed of only some of the transducer elements of the ultrasound probe, the transmitter 1031 may perform a plurality of ultrasound transmission sessions while changing the transducer elements of the ultrasound probe included in transmission transducer element array each time, the first adder 1048 may generate the first acoustic line signal for each of the measurement points by synthesizing a plurality of first acoustic line signals for the measurement point, each of which acquired based on one of the ultrasound transmission sessions, and the second adder 1048 may generate the second acoustic line signal for each of the measurement points by synthesizing a plurality of second acoustic line signals for the measurement point, each of which acquired based on one of the ultrasound transmission sessions.

In the ultrasound signal processing device pertaining to one aspect of the present disclosure, the transmitter 1031 may perform a plurality of ultrasound transmission sessions until all of the transducer elements of the ultrasound probe have transmitted ultrasound at least once.

One aspect of the present disclosure is an ultrasound diagnostic device configured so that the ultrasound probe 101 is connectable thereto.

This achieves an ultrasound diagnostic device capable of generating high quality ultrasound images having higher resolution and less noise over the entirety of an ultrasound irradiation area than conventional technology.

SUPPLEMENT

Each of the embodiments and modifications described above should be construed as being a preferable and specific example of implementation of the technology pertaining to the present disclosure. As such, any value, any shape, any material, any constituent element, any position of any constituent element, any connection of any constituent element, any step, and any order in which any step is performed shall be construed as being a non-limiting example. Further, among the constituent elements described in the embodiments and modifications, any constituent element not recited in the independent claim, which represents the broadest concept of the present disclosure, shall be construed as a constituent element not necessarily essential but included in a preferable form of implementation of the technology pertaining to the present disclosure.

Further, in order to facilitate understanding, constituent elements described in the embodiments and the modifications may be illustrated in drawings at a scale differing from their actual sizes. Further, the present invention shall not be construed as being limited to the embodiments and the modification, and instead, shall be construed as encompassing any modification that does not depart from the spirit and the scope of the present disclosure.

Further, the embodiments and modifications do not provide description of circuit parts and lead wires disposed on substrates in ultrasound diagnostic devices. This is since various forms of electric wiring and electric circuitry are implementable based on knowledge possessed by a skilled artisan in the present field of technology, and are not directly essential in describing the technology pertaining to the present disclosure. Further, all drawings referred to in the above are schematic drawings and may not be accurate in a strict sense.

Although the technology pertaining to the present disclosure has been fully described by way of examples with reference to the accompanying drawings, it is to be noted that various changes and modifications will be apparent to those skilled in the art. Therefore, unless such changes and modifications depart from the scope of the present disclosure, they should be construed as being included therein.

What is claimed is:

1. An ultrasound signal processing device that causes an ultrasound probe having a plurality of transducer elements to transmit ultrasound towards a living subject to acquire ultrasound reflected from the inside of the living subject and generates a reception signal from the reflected ultrasound, the ultrasound signal processing device comprising:
    an ultrasound signal processing circuit that functions as:
    a transmitter performing a plurality of ultrasound transmission sessions, each of the sessions causing a transmission transducer element array composed of some of the transducer elements to transmit ultrasound, each of sessions having a different transmission transducer element array;
    a receiver generating a plurality of reception signal sequences, each of the reception signal sequences generated for each of the transducer elements based on reflected ultrasound that the each of the transducer elements receives in response to the transmission of the ultrasound;
    a first reception aperture setter designating a first reception transducer element array including first reception transducer elements composed of some of the transducer elements and having a center position corresponding to a center position of the transmission transducer element array;
    a transmission time calculator performing, for each of a plurality of predetermined measurement points arranged within an assumed area of reach of the ultrasound inside the living subject, a calculation of transmission time that is a time period from transmission of the ultrasound until arrival of the ultrasound at the each of the plurality of the predetermined measurement points;
    a first reception time calculator performing, for the each of the plurality of the predetermined measurement points, a calculation of reception time for each of the first reception transducer elements in the first reception transducer element array, the reception time being a time period from reflection of the ultrasound at the each of the plurality of the predetermined measurement points until arrival of the ultrasound at the each of the first reception transducer elements;
    a first delay amount calculator performing, for the each of the plurality of the predetermined measurement points, (i) a calculation of total propagation time for each of the first reception transducer elements, the total propagation time being a sum of the transmission time and the reception time for the each of the first reception transducer elements, and (ii) a calculation of a delay amount for each first reception transducer element based on the total propagation time for the each of the first reception transducer elements;
    a first delay processor performing, for the each of the plurality of the predetermined measurement points, a specification of a reception signal value for each first reception transducer element, the specified reception signal value being a reception signal value corresponding to the delay amount for the first reception transducer element, from among reception signal values composing one of the reception signal sequences that corresponds to the first reception transducer element;

a first adder generating a first acoustic line signal for the each of the plurality of the predetermined measurement points, based on the specified reception signal values for the first reception transducer elements specified with respect to the each of the plurality of the predetermined measurement points, by synthesizing a plurality of first acoustic line signals for the each of the plurality of the predetermined measurement points, each of which is acquired based on one of the ultrasound transmission sessions;

a second reception aperture setter performing, for the each of the plurality of the predetermined measurement points, a designation of a second reception transducer element array including second reception transducer elements composed of some of the transducer elements and having a center position corresponding to one of the transducer elements that is closest to the each of the plurality of the predetermined measurement points;

a second reception time calculator performing, for the each of the plurality of the predetermined measurement points, a calculation of reception time for each of the second reception transducer elements in the second reception transducer element array, the reception time being a time period from reflection of the ultrasound at the each of the plurality of the predetermined measurement points until arrival of the ultrasound at the each of the second reception transducer elements;

a second delay amount calculator performing, for the each of the plurality of the predetermined measurement points, (i) a calculation of total propagation time for each of the second reception transducer elements, the total propagation time being a sum of the transmission time and the reception time for the each of the second reception transducer elements, and (ii) a calculation of a delay amount for each second reception transducer element based on the total propagation time for the each of the second reception transducer elements;

a second delay processor performing, for the each of the plurality of the predetermined measurement points, a specification of a reception signal value for each second reception transducer element, the specified reception signal value being a reception signal value corresponding to the delay amount for the second reception transducer element, from among reception signal values composing one of the reception signal sequences that corresponds to the second reception transducer element;

a second adder generating a second acoustic line signal for the each of the plurality of the predetermined measurement points, based on the specified reception signal values for the second reception transducer elements specified with respect to the each of the plurality of the predetermined measurement points, by synthesizing a plurality of second acoustic line signals for the each of the plurality of the predetermined measurement points, each of which is acquired based on one of the ultrasound transmission sessions;

a Tx/Rx selection signal calculator selecting either to generate an ultrasound image based on the first acoustic line signal or to generate the ultrasound image based on the second acoustic line signal; and an outputter that outputs for generating the ultrasound image either the first acoustic line signal or the second acoustic line signal in accordance with the result of the selection by the Tx/Rx selection signal calculator.

2. The ultrasound signal processing device of claim 1, wherein the ultrasound signal processing circuit also functions as:

a first weight calculator calculating a weight sequence for the first reception transducer element array, the weight sequence including the greatest weight for the one of the first reception transducer elements at the center position of the first reception transducer element array, and the first adder generates the first acoustic signal line for the each of the plurality of the predetermined measurement points by, for the each of the first reception transducer element, multiplying the specified reception signal value for the first reception transducer element specified with respect to the each of the plurality of the predetermined measurement points by a weight included in the weight sequence that corresponds to the first reception transducer element, and by summing products yielded by performing the multiplication for each first reception transducer element.

3. The ultrasound signal processing device of claim 1, wherein, the ultrasound signal processing circuit also functions as:

a second weight calculator calculating a weight sequence for the second reception transducer element array, the weight sequence including the greatest weight for the one of the second reception transducer elements at the center position of the second reception transducer element array, and the second adder generates the second acoustic signal line for the each of the plurality of the predetermined measurement points by, for each second reception transducer element, multiplying the specified reception signal value for the second reception transducer element specified with respect to the each of the plurality of the predetermined measurement points by a weight included in the weight sequence that corresponds to the second reception transducer element, and by summing products yielded by performing the multiplication for each second reception transducer element.

4. The ultrasound signal processing device of claim 1, wherein the Tx/Rx selection signal calculator selects one of the first acoustic line signal and the second acoustic line signal.

5. The ultrasound signal processing device of claim 4, wherein the Tx/Rx selection signal calculator performs the selection based on input performed by an operator of the ultrasound signal processing device or based on a predetermined condition.

6. The ultrasound signal processing device of claim 4, wherein the Tx/Rx selection signal calculator performs the selection based on a characteristic of the plurality of reception signal sequences.

7. The ultrasound signal processing device of claim 6, wherein the Tx/Rx selection signal calculator determines whether or not a puncture needle is being used with respect to the living subject and selects the first acoustic line signal when determining that a puncture needle is being used with respect to the living subject.

8. The ultrasound signal processing device of claim 6, wherein
the Tx/Rx selection signal calculator, when detecting an object causing specular reflection based on the plurality of reception signal sequences, determines that a puncture needle is being used with respect to the living subject and selects the first acoustic line signal.

9. The ultrasound signal processing device of claim 4, wherein
the Tx/Rx selection signal calculator performs the selection based on at least one of the first acoustic line signal and the second acoustic line signal.

10. The ultrasound signal processing device of claim 1, wherein
the Tx/Rx weight calculator calculating a weight for the first acoustic line signal and a weight for the second acoustic line signal; and
the ultrasound signal processing circuit also functions as an output mixer performing a calculation of multiplying each of the first acoustic line signal and the second acoustic line signal by a corresponding weight and summing the products yielded by performing the multiplication with respect to each of the first acoustic line signal and the second acoustic line signal, and outputting a result of the calculation.

11. The ultrasound signal processing device of claim 10, wherein
the Tx/Rx weight calculator performs, for the each of the plurality of the predetermined measurement points, a calculation of the weight corresponding to the first acoustic line signal and the weight corresponding to the second acoustic line signal based on input performed by an operator of the ultrasound signal processing device or based on a predetermined condition.

12. The ultrasound signal processing device of claim 10, wherein
the Tx/Rx weight calculator calculates the weight corresponding to the first acoustic line signal and the weight corresponding to the second acoustic line signal based on a characteristic of the plurality of reception signal sequences.

13. The ultrasound signal processing device of claim 10, wherein
the Tx/Rx weight calculator calculates the weight corresponding to the first acoustic line signal and the weight corresponding to the second acoustic line signal based on the first acoustic line signal and the second acoustic line signal.

14. The ultrasound signal processing device of claim 6, wherein
the characteristic of the plurality of reception signal sequences is calculated based on the reception signal value for the one of the first reception transducer elements with the smallest delay amount in the first reception transducer element array and the reception signal value for the one of the second reception transducer elements with the smallest delay amount in the second transducer element array.

15. The ultrasound signal processing device of claim 1, wherein
the transmitter performs a plurality of ultrasound transmission sessions until all of the transducer elements of the ultrasound probe have transmitted ultrasound at least once.

16. The ultrasound signal processing device of claim 1, wherein
the transmitter performs a plurality of ultrasound transmission sessions until all of the transducer elements of the ultrasound probe have transmitted ultrasound at least once.

17. An ultrasound diagnostic device comprising
the ultrasound signal processing device of claim 1, wherein
the ultrasound signal processing device is configured so that the ultrasound probe is connectable thereto.

18. An ultrasound diagnostic device that causes an ultrasound probe having a plurality of transducer elements to transmit ultrasound towards a living subject to acquire ultrasound reflected from the inside of the living subject and generates a reception signal from the reflected ultrasound, the ultrasound signal processing device comprising:
a transmitter performing a plurality of ultrasound transmission sessions of causing a transmission transducer element array composed of some of the transducer elements to transmit ultrasound while changing the transducer elements included in transmission transducer element array each time;
a receiver generating a plurality of reception signal sequences, each of the reception signal sequences generated for each of the transducer elements based on reflected ultrasound that a corresponding one of the transducer elements receives in response to the transmission of the ultrasound;
a first reception beam former which i) designates a first reception transducer element array including first reception transducer elements composed of some of the transducer elements and having a center position corresponding to a center position of the transmission transducer element array, ii) calculates, for each of a plurality of predetermined measurement points, a delay amount for each first reception transducer element, iii) performs, for the each of the plurality of the predetermined measurement points, a specification of a reception signal value for each first reception transducer element, the specified reception signal value being a reception signal value corresponding to the delay amount for the first reception transducer element, from among reception signal values composing one of the reception signal sequences that corresponds to the first reception transducer element, and iv) generates a first acoustic line signal for the each of the plurality of the predetermined measurement points, based on the specified reception signal values for the first reception transducer elements specified with respect to the each of the plurality of the predetermined measurement points, by synthesizing a plurality of first acoustic line signals for the each of the plurality of the predetermined measurement points, each of which acquired based on one of the ultrasound transmission sessions;
a second reception beam former which v) designates, for the each of the plurality of the predetermined measurement points, a second reception transducer element array including second reception transducer elements composed of some of the transducer elements and having a center position corresponding to one of the transducer elements that is closest to the each of the plurality of the predetermined measurement points, vi) calculates, for the each of the plurality of the predetermined measurement points, a delay amount for each second reception transducer element, vii) performs, for the each of the plurality of the predetermined measurement points, a specification of a reception signal value for each second reception transducer element, the specified reception signal value being a reception signal value corresponding to the delay amount for the second reception transducer element, from among reception signal values composing one of the reception signal sequences that corresponds to the second reception transducer element, and viii) generates a second acoustic line signal for the each of the plurality of the predetermined measurement points, based on the specified reception signal values for the second reception transducer elements specified with respect to the each of the plurality of the predetermined measurement points, by synthesizing a plurality of second acoustic line signals for the each of the plurality of the predetermined measurement points, each of which acquired based on one of the ultrasound transmission sessions;

an image generator which generates an image based on signals from the first reception beam former or the second reception beam former; and a Tx/Rx selector which selects either to output for generating the image, signals from the first reception beam former to the image generator or to output for generating the image, signals from the second reception beam former to the image generator.

19. The ultrasound signal processing device of claim 1, wherein both the first acoustic line signal and the second acoustic line signal are generated for generating the ultrasound image from the same ultrasound transmission sessions, and the outputter outputs only one of the first acoustic line signal and the second acoustic line signal for generating the ultrasound image.

20. The ultrasound signal processing device of claim 18, wherein both the first acoustic line signal and the second acoustic line signal are generated for generating the ultrasound image from the same ultrasound transmission sessions, and the outputter outputs only one of the first acoustic line signal and the second acoustic line signal for generating the ultrasound image.

* * * * *